United States Patent
Chen et al.

(10) Patent No.: US 11,180,804 B2
(45) Date of Patent: Nov. 23, 2021

(54) IN SITU ATAC SEQUENCING

(71) Applicants: Massachusetts Institute of Technology, Cambridge, MA (US); President and Fellows of Harvard College, Cambridge, MA (US)

(72) Inventors: Fei Chen, Cambridge, MA (US); Andrew C. Payne, Cambridge, MA (US); Jason D. Buenrostro, Cambridge, MA (US); Paul Reginato, Cambridge, MA (US); Edward Stuart Boyden, Chestnut Hill, MA (US); Shahar Alon, Cambridge, MA (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 441 days.

(21) Appl. No.: 16/043,950

(22) Filed: Jul. 24, 2018

(65) Prior Publication Data
US 2019/0032128 A1  Jan. 31, 2019

Related U.S. Application Data

(60) Provisional application No. 62/536,628, filed on Jul. 25, 2017.

(51) Int. Cl.
*C12P 19/34* (2006.01)
*C12Q 1/6874* (2018.01)
(Continued)

(52) U.S. Cl.
CPC ....... *C12Q 1/6874* (2013.01); *C12N 15/1065* (2013.01); *C12N 15/1082* (2013.01); *C12Q 1/6809* (2013.01); *C12Q 1/6869* (2013.01)

(58) Field of Classification Search
CPC .......................... C12Q 1/6874; C12N 15/1065
See application file for complete search history.

(56) References Cited

U.S. PATENT DOCUMENTS

| 5,952,232 A | 9/1999 | Rothman |
| 6,107,081 A | 8/2000 | Feeback et al. |
| (Continued) | | |

FOREIGN PATENT DOCUMENTS

| CN | 104350372 A | 2/2015 |
| JP | 2005291759 A | 10/2005 |
| (Continued) | | |

OTHER PUBLICATIONS

Office Action dated Apr. 4, 2018 from U.S. Appl. No. 14/627,310, filed Feb. 20, 2015.
(Continued)

*Primary Examiner* — Kenneth R Horlick
(74) *Attorney, Agent, or Firm* — Elmore Patent Law Group, P.C.; Joseph Zucchero; Carolyn Elmore

(57) ABSTRACT

The present invention provides methods for analyzing polynucleotides such as genomic DNA. In some embodiments, the disclosure provides a method for preparing and amplifying a genomic DNA library in situ in a fixed biological sample. The method comprises treating a fixed biological sample with an insertional enzyme complex to produce tagged fragments of genomic DNA. The method further comprises circularizing the tagged fragments of genomic DNA. The method further comprises amplifying the tagged fragments of genomic DNA.

19 Claims, 13 Drawing Sheets

HeLa

Primary neuron culture

IMR90

(51) Int. Cl.
*C12N 15/10* (2006.01)
*C12Q 1/6809* (2018.01)
*C12Q 1/6869* (2018.01)

(56) References Cited

U.S. PATENT DOCUMENTS

| | | |
|---|---|---|
| 6,271,278 B1 | 8/2001 | Park et al. |
| 6,287,870 B1 | 9/2001 | Wardlaw et al. |
| 10,059,990 B2 | 8/2018 | Boyden et al. |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,526,649 B2 * | 1/2020 | Chen .............. C12Q 1/6841 |
| 10,774,367 B2 * | 9/2020 | Fraser ............. C12Q 1/6806 |
| 2002/0176880 A1 | 11/2002 | Cruise et al. |
| 2003/0120231 A1 | 6/2003 | Wang et al. |
| 2004/0137527 A1 | 7/2004 | Sleytr et al. |
| 2004/0248326 A1 | 12/2004 | Ziaie et al. |
| 2005/0034990 A1 | 2/2005 | Crooks et al. |
| 2005/0090016 A1 | 4/2005 | Rich et al. |
| 2005/0169962 A1 | 8/2005 | Bhatia et al. |
| 2005/0196702 A1 | 9/2005 | Bryant et al. |
| 2006/0000767 A1 | 1/2006 | Trauger et al. |
| 2006/0003356 A1 | 1/2006 | Shaw et al. |
| 2006/0110760 A1 | 5/2006 | Kim et al. |
| 2006/0115146 A1 | 6/2006 | Ogura et al. |
| 2006/0165912 A1 | 7/2006 | Koberstein et al. |
| 2007/0023942 A1 | 2/2007 | Andino et al. |
| 2007/0042954 A1 | 2/2007 | Chen et al. |
| 2007/0134902 A1 | 6/2007 | Bertino et al. |
| 2008/0261834 A1 | 10/2008 | Simon et al. |
| 2008/0286360 A1 | 11/2008 | Shoichet et al. |
| 2009/0011141 A1 | 1/2009 | Carter et al. |
| 2009/0011420 A1 | 1/2009 | Barron et al. |
| 2009/0096133 A1 | 4/2009 | Doyle et al. |
| 2009/0191627 A1 | 7/2009 | Fadeev et al. |
| 2009/0241681 A1 | 10/2009 | Machauf et al. |
| 2010/0041128 A1 | 2/2010 | Banes et al. |
| 2010/0055161 A1 | 3/2010 | Ahn |
| 2010/0056445 A1 | 3/2010 | Sharma et al. |
| 2010/0068725 A1 | 3/2010 | Armbruster et al. |
| 2010/0096334 A1 | 4/2010 | Edmiston et al. |
| 2010/0119755 A1 | 5/2010 | Chung et al. |
| 2011/0070604 A1 | 3/2011 | Gimzewski et al. |
| 2011/0087315 A1 | 4/2011 | Richardson-Burns et al. |
| 2011/0091717 A1 | 4/2011 | Weiss et al. |
| 2011/0091922 A1 | 4/2011 | Krishnan et al. |
| 2011/0291357 A1 | 12/2011 | Boyle |
| 2012/0025271 A1 | 2/2012 | Nakano |
| 2012/0184670 A1 | 7/2012 | Kobayashi et al. |
| 2012/0220478 A1 | 8/2012 | Shaffer |
| 2012/0251527 A1 | 10/2012 | Reiser |
| 2012/0310223 A1 | 12/2012 | Knox et al. |
| 2013/0045503 A1 | 2/2013 | Miyawaki et al. |
| 2013/0203605 A1 * | 8/2013 | Shendure .......... C12N 15/1093 506/2 |
| 2014/0087139 A1 | 3/2014 | Rowley et al. |
| 2014/0193651 A1 | 7/2014 | Kharlampieva et al. |
| 2014/0364330 A1 | 12/2014 | Mershin et al. |
| 2015/0353989 A1 * | 12/2015 | Fraser ............. C12Q 1/6806 506/26 |
| 2015/0370961 A1 | 12/2015 | Zhang et al. |
| 2015/0376261 A1 | 12/2015 | Steyaert et al. |
| 2016/0116384 A1 | 4/2016 | Boyden et al. |
| 2016/0252528 A1 | 9/2016 | Sangaralingham et al. |
| 2016/0265046 A1 * | 9/2016 | Zhang .............. C12Q 1/6846 |
| 2016/0304952 A1 | 10/2016 | Boyden et al. |
| 2016/0305856 A1 | 10/2016 | Chen et al. |
| 2017/0067096 A1 | 3/2017 | Wassie et al. |
| 2017/0081489 A1 | 3/2017 | Boyden et al. |
| 2017/0089811 A1 | 3/2017 | Chen et al. |
| 2018/0119219 A1 * | 5/2018 | Chen ............... C12Q 2545/113 |
| 2019/0071656 A1 * | 3/2019 | Chang ............... C12N 15/90 |

FOREIGN PATENT DOCUMENTS

| | | |
|---|---|---|
| JP | 2006036957 A | 2/2006 |
| JP | 2008286694 A | 11/2008 |
| JP | 2009191125 A | 8/2009 |
| JP | 2014005231 A | 1/2014 |
| WO | 0008212 A1 | 2/2000 |
| WO | 2008058302 A1 | 5/2008 |
| WO | 2010048605 A1 | 4/2010 |
| WO | 2012142664 A1 | 10/2012 |
| WO | 2014025392 A1 | 2/2014 |
| WO | 2014152984 A1 | 9/2014 |
| WO | 2015041755 A1 | 3/2015 |
| WO | 2015127183 A2 | 8/2015 |
| WO | 2017027367 A1 | 2/2017 |
| WO | 2017027368 A1 | 2/2017 |
| WO | 2017079406 A1 | 5/2017 |
| WO | 2017147435 A1 | 8/2017 |
| WO | 2018157074 A1 | 8/2018 |
| WO | 2019144391 A1 | 8/2019 |

OTHER PUBLICATIONS

Bleckmann, J. et al., "Surface-Layer Lattices as Patterning Element for Multimeric Extremozymes", Small Journal, 2013, 1-8.

Breitwieser, A. et al., "Magnetic Beads Functionalized with Recombinant S-Layer Protein Exhibit High Human IgG-Binding and Anti-Fouling Properties", Current Topics in Peptide & Protein Research, vol. 17, 2016, 45-55.

Gyorvary, E. S. et al., "Self-Assembly and Recrystallization of Bacterial S-Layer Proteins at Silicon Supports Imaged in Real Time by Atomic Force Microscopy", Journal of Microscopy, vol. 212, 2003, 300-306.

Hoffman, T. L. et al., "A Biosensor Assay for Studying Ligand-Membrane Receptor Interactions: Binding of Antibodies and HIV-1 Envto Chemokine Receptors", PNAS, 97(21), 2000, 11215-11220.

Ke, Rongqin et al., "Supplementary Material In situ sequencing for RNA analysis in preserved tissue and cells", Nature Methods 10(9):857-60, 2013, 1-29.

Pum, D. et al., "Reassembly of S-Layer Proteins", Nanotechnology, 2014, 1-15.

Rothbauer, M. et al., "Exploitation of S-Layer Anisotropy: pH-Dependent Nanolayer Orientation for Cellular Micropatterning,", Acs NANO, published online, 2013.

Sleytr, U. et al., "Heterologous Reattachment of Regular Arrays of Glycoproteins on Bacterial Surfaces", Nature, vol. 257, 1975, 400-401.

Sleytr, U. et al., "S-Layers Principles and Applications", FEMS Microbiology Rev., 2014, 1-42.

Zhang, R. et al., "Tools for GPCR Drug Discovery", Acta Pharmacologica Sinica, 33, 2012, 372-384.

"Epitope Recovery Methods for IHC", Nov. 7, 2015, ThermoFisher Scientific, pp. 1-2.

Al, H. et al., "Exploration of new chromophore structures leads to the identification of improved blue fluorescent proteins", Biochemistry, 46, 2007, 5904-10.

Bates, M. et al., "Multicolor super-resolution imaging with photo-switchable fluorescent probes", Science, 317, 2007, 1749-1753.

Batish, M. et al., "Neuronal mRNAs Travel Singly into Dendrites", PNAS, vol. 109(12), 2012, 4645-4650.

Beliveau, B. et al., "Versatile design and synthesis platform for visualizing genomes with Oligopaint FISH probes", PNAS, vol. 109(52): pfa, 2012, 21301-21306.

Bokman, S. H. et al., "Renaturation of Aequorea gree-fluorescent protein", Biochem. Biophys. Res. Commun., 101, 1981, 1372-80.

Bossi, M. et al., "Multicolor far-field fluorescence nanoscopy through isolated detection of distinct molecular species", Nano Lett., 8, 2008, 2463-8.

Bruchez, M. et al., "Semiconductor nanocrystals as fluorescent biological labels", Science, vol. 281, 1998, 2013-6.

Buckley, P. et al., "Cytoplasmic Intron Sequence-Retaining Transcripts Can Be Dendritically Targeted via ID Element Retrotransposons", Neuron, vol. 69, 2011, 877-884.

(56) References Cited

OTHER PUBLICATIONS

Buenrostro, J. D. et al., "ATAC-seq: A Method for Assaying Chromatin Accessibility Genome-Wide : ATAC-seq for Assaying Chromatin Accessibility", In: "Current Protocols in Molecular Biology", Wiley, New York, NY, Jan. 5, 2015.
Buxbaum, A. et al., "Single-Actin mRNA Detection in Neurons Reveals a Mechanism for Regulating Its Translatability", Science, vol. 343, 2014, 419-422.
Cabili, M. et al., "Localization and abundance analysis of human lncRNAs at single-cell and single-molecule resolution", Genome Biology, vol. 16(20), 2015.
Cai, et al., Nat Meth., 10, 2013, 540-547.
Cajigas, I. et al., "The local transcriptome in the synaptic neuropil revealed by deep sequencing and high-resolution imaging", Neuron 74, 2012, 453-466.
Cao, W. , "DNA ligases and ligase-based technologies", Clinical and Applied Immunology Reviews, Elsevier, Amsterdam, NL, vol. 2, No. 1, Jan. 15, 2001, 33-43.
Carpenter, A. E. et al., "CellProfiler: image analysis software for identifying and quantifying cell phenotypes", Genome Biol., 7, 2006, R100.
Chang, J-B et al., "Iterative expansion microscopy", Nature Methods, 14(6), Jun. 2017, 593-599.
Chen, F. et al., "Expansion Microscopy", Science, 347(6621):, Jan. 15, 2015, 1-18.
Chen, F. et al., "Nanoscale Imaging of RNA with Expansion Microscopy", Nature Methods, 13(8):, Aug. 2016, 679-684.
Chen, F. et al., "Supplementary Material for Expansion Microscopy", Science, 347(6221), Jan. 15, 2015, 543-548.
Chen, K. et al., "Spatially resolved, highly multiplexed RNA profiling in single cells", Science. vol. 348(6233), 2015, aaa6090-aaa6090.
Chen, X. et al., "[Supplementary material] ATAC-see reveals the accessible genome by transposase-mediated imaging and sequencing", Nature Methods, vol. 13, No. 12, Oct. 17, 2016, 1813-1828.
Choi, H. et al., "Next-Generation in Situ Hybridization Chain Reaction: Higher Gain, Lower Cost, Greater Durability", ACS Nano 8(5), 2014, 4284-4294.
Choi, H. et al., "Programmable in situ amplification for multiplexed imaging of mRNA expression", Nature Biotechnology, 28(11), 2010, 1208-1212.
Chozinski, T. et al., "Expansion microscopy with conventional antibodies and fluorescent proteins", Nature Methods, vol. 13(6), 2016, 485-491.
Chu, J. et al., "Non-invasive intravital imaging of cellular differentiation with a bright red-excitable fluorescent protein", Nat. Methods, 11, 2014, 572-8.
Clemson, C. et al., "An architectural role for a nuclear noncoding RNA: NEAT1 RNA is essential for the structure of paraspeckles", Molecular Cell, 33, 2009, 717-26.
Cormack, B. P. et al., "FACS-optimized mutants of the green fluorescent protein (GFP)", Gene, 173, 1996, 33-8.
Cubitt, A. B. et al., "Understanding structure-function relationships in the Aequorea victoria green fluorescent protein", Methods Cell Biol., 58, 1999, 19-30.
Dedecker, P. et al., "Localizer: fast, accurate, open-source, and modular software package for superresolution microscopy", J. Biomed. Opt., 17, 2012, 126008.
Edelstein, A. et al., "Computer control of microscopes using μManager", Curr. Protoc. Mol. Biol. Chapter 14, Unit14.20, 2010.
English, B. P. et al., "A three-camera imaging microscope for high-speed single-molecule tracking and super-resolution imaging in living cells", in SPIE Nanosci. + Eng. (Mohseni, H., Agahi, M. H. & Razeghi, M.) 955008 (International Society for Optics and Photonics, 2015). doi: 10.1117/12.2190246,.
Engreitz, J. et al., "The Xist lncRNA exploits three-dimensional genome architecture to spread across the X chromosome", Science 341, 2013, 1237973.
Femino, A. et al., "Visualization of Single RNA Transcripts in Situ", Science, vol. 280, 1998, 585-590.

Feng, G. et al., "Imaging neuronal subsets in transgenic mice expressing multiple spectral variants of GFP", Neuron, 28, 2000, 41-51.
Filonov, G. S. et al., "Bright and stable near-infrared fluorescent protein for in vivo imaging", Nat. Biotechnol., 29, 2011, 757-61.
Fouz, M. et al., "Bright Fluorescent Nanotags from Bottlebrush Polymers with DNA-Tipped Bristles", ACS Central Science, vol. 1, 2015, 431-438.
Freifeld, L. et al., "Expansion microscopy of zebrafish for neuroscience and developmental biology studies", PNAS (online), Nov. 21, 2017, E10799-E10808.
Goedhardt, J. et al., "Structure-guided evolution of cyan fluorescent proteins towards a quantum yield of 93%", Nat. Commun., 3, 2012, 751.
Griesbeck, O. et al., "Reducing the environmental sensitivity of yellow fluorescent protein. Mechanism and applications", J. Biol. Chem., 276, 2001, 29188-94.
Gurskaya, N. G. et al., "Engineering of a monomeric green-to-red photoactivatable fluorescent protein induced by blue light", Nat. Biotechnol., 24, 2006, 461-5.
Habuchi, S. et al., "mKikGR, a monomeric photoswitchable fluorescent protein", PLoS One, 3, 2008, e3944.
Hackstadt, T. , "Steric hindrance of antibody binding to surface proteins of Coxiella burnetti by phase I lipopolysaccharide", Infect Immun, 56, 1998, 802-807.
Heim, R. et al., "Engineering green fluorescent protein for improved brightness, longer wavelengths and fluorescence resonance energy transfer", Curr. Biol., 6, 1996, 178-82.
Heim, R. et al., "Wavelength mutations and posttranslational autoxidation of green fluorescent protein", Proc. Natl. Acad. Sci. U.S.A., 91, 1994, 12501-4.
Huang, B. et al., "Whole-cell 3D STORM reveals interactions between cellular structures with nanometer-scale resolution", Nat. Methods, 5, 2008, 1047-1052.
Huisken, J. et al., "Optical Sectioning Deep Inside Live Embryos by Selective Plane Illumination Microscopy", Science. vol. 305, 2004, 1007-1009.
Hunt, et al., "High temperature antigen retrieval and loss of nuclear morphology: a comparison of microwave\rand autoclave techniques", J. Clin. Pathol. 49, 1996, 767-770.
Jekel, P A. et al., "Use of endoproteinase Lys-C from Lysobacter enzymogenes in protein sequence analysis", Anal. Biochem., 134, 1983, 347-354.
Jimenez, N. et al., "A Novel Approach for Intracellular 3D Immuno-Labeling for Electron Tomography", Traffic,13, 2012, 926-933.
Jung, H. et al., "Axonal mRNA localization and local protein synthesis in nervous system assembly, maintenance and repair", Nat. Rev. Neurosci., vol. 13(5), 2012, 308-24.
Kakimoto, K. et al., "Hypothesis for the mechanism for heat-induced antigen retrieval occurring on fresh frozen sections without formalin-fixation in immunohistochemistry", J Mol Histol., 39, 2008, 389-399.
Kaur, et al., Biochemistry 45, 2006, 7347-7355.
Ke, R. et al., "In situ sequencing for RNA analysis in preserved tissue and cells", Nature Methods, vol. 10(9), 2013, 857-60.
Laemmli, U. K. , "Cleavage of structural proteins during the assembly of the head of bacteriophage T4", Nature, 227, 1970, 680-685.
Lam, A. J. et al., "Improving FRET dynamic range with bright green and red fluorescent proteins", Nat. Methods, 9, 2012, 1005-12.
Lee, J. H. et al., "Highly Multiplexed Subcellular RNA Sequencing in Situ", Sciencexpress, online http://www.sciencemag.org/content/early/recent, 6 pages, This may be the same as Lee (FIP Ref No. 304851), Feb. 27, 2014.
Lein, E. et al., "Genome-wide atlas of gene expression in the adult mouse brain", Nature, vol. 445, 2007, 168-76.
Levsky, J. et al., "Fluorescence in situ hybridization: past, present and future", Journal of Cell Science, 116, 2003, 2833-2838.
Lieberman-Aiden, E. et al., "Comprehensive mapping of long-range interactions reveals folding principles of the human genome", Science 326, 2009, 289-93.

(56) References Cited

OTHER PUBLICATIONS

Livet, J. et al., "Transgenic strategies for combinatorial expression of fluorescent proteins in the nervous system", Nature, 450, 2007, 56-62.
Lowe, D. G. , "Distinctive Image Features from Scale-Invariant Keypoints", Int. J. Comput. Vis., 60, 2004, 91-110.
Lubeck, E. et al., "Single-cell in situ RNA profiling by sequential hybridization", Nature Methods, vol. 11(4), 2014, 360-1.
Lubeck, E. et al., "Single-cell systems biology by super-resolution imaging and combinatorial labeling", Nature Methods, vol. 9, 2012, 743-8.
Markwardt, M. L. et al., "An improved cerulean fluorescent protein with enhanced brightness and reduced reversible photoswitching", PLoS One, 6, 2011, e17896.
Mckinney, S. A. et al., "A bright and photostable photoconvertible fluorescent protein", Nat. Methods, 6, 2009, 131-3.
Mito, M. et al., "Simultaneous multicolor detection of RNA and proteins using super-resolution microscopy", Methods, doi:10.1016/j.ymeth.2015.11.007., 2015.
Mortensen, K. I. et al., "Optimized localization analysis for singlemolecule tracking and super-resolution microscopy", Nat. Methods, 7, 2010, 377-81.
Nagai, T. et al., "A variant of yellow fluorescent protein with fast and efficient maturation for cell-biological applications", Nat. Biotechnol., 20, 2002, 87-90.
Nagre, R. D. et al., "Thermosaline Resistant Acrylamide-Based Polyelectrolyte as Filtration Control Additive in Aqueous-Based Mud", Petroleum and Coal, vol. 56, No. 3, 2014, 222-230.
Nilsson, M. et al., "RNA-templated DNA ligation for transcript ananlysis", Nucleic Acids Research, Information Retrieval LTD., vol. 29, No. 2, Jan. 15, 2001, 578-581.
Ormo, M. et al., "Crystal structure of the Aequorea victoria green fluorescent protein", Science, 273, 1996, 1392-5.
Panning, B. et al., "X chromosome Inactivation is Mediated by by Xist RNA stabilization", Cell. vol. 90, 1997, 907-16.
Park, Y. N. et al., "Detection of Hepatitis C Virus RNA Using Ligation-Dependent Polymerase Chain Reaction in Formalin-Fixed, Paraffin-Embedded Liver Tissues", Amer. J. of Pathol., vol. 149, No. 5, Nov. 1, 1996, 1485-1491.
Plath, K. et al., "Xist RNA and the mechanism of X chromosome inactivation", Annu. Rev. Genet. 36, 2002, 233-78.
Raj, A. et al., "Detection of individual endogenous RNA transcripts in situ using multiple singly labeled probes", Methods in Enzymology, vol. 472 (Elsevier Inc.), 2010, 365-386.
Raj, A. et al., "Imaging individual mRNA molecules using multiple singly labeled probes", Nat. Methods 5(10), 2008, 877-879.
Randall, K. J. et al., "A dual-label technique for the immunohistochemical demonstration of T-lymphocyte subsets in formalin-fixed, paraffin-embedded rat lymphoid tissue", Toxicol. Pathol., 36, 2008, 795-804.
Rego, E. H. et al., "Nonlinear structured-illumination microscopy with a photoswitchable protein reveals cellular structures at 50-nm resolution", Proc. Natl. Acad. Sci. U.S.A., 109, 2012, E135-43.
Reinhart-King, C. A. et al., "Dynamics and Mechanics of EndothelialCell Spreading", Biophysical J, 89(1):, Jul. 1, 2005, 676-689.
Rose, R. et al., "Ocular ascorbate transport and metabolism", A. Comp. Physiol.,100, 1991, 273-85.
Schindelin, J. et al., "Fiji: an open-source platform for biological-image analysis", Nature Methods, vol. 9, 2012, 676-82.
Schnell, U. et al., "Immunolabeling artifacts and the need for live-cell imaging", Nat. Methods, 9, 2012, 152-158.
Seneviratne, U. et al., "S-nitrosation of proteins relevant to Alzheimer's disease during early stages of neurodegeneration", Proc. Natl. Acad. Sci. U. S. A. 1521318113—(2016). doi:10.1073/pnas.1521318113.
Shah, S. et al., "Single-molecule RNA detection at depth via hybridization chain reaction and tissue hydrogel embedding and clearing", Development In Review, 2016.
Shaner, N. C. et al., "Improved monomeric red, orange and yellow fluorescent proteins derived from Discosoma sp. red fluorescent protein", Nat. Biotechnol., 22, 2004, 1567-72.
Shaner, N. C. et al., "Improving the photostability of bright monomeric orange and red fluorescent proteins", Nat. Methods, 5, 2008, 545-51.
Shcherbakova, D. M. , "An orange fluorescent protein with a large Stokes shift for single-excitation multicolor FCCS and FRET imaging", J. Am. Chem. Soc., 134, 2012, 7913-23.
Shcherbo, D. et al., "Far-red fluorescent tags for protein imaging in living tissues", Biochem. J., 418, 2009, 567-74.
Sniegowski, J. A. et al., "Maturation efficiency, trypsin sensitivity, and optical properties of Arg96, Glu222, and Gly67 variants of green fluorescent protein", Biochem. Biophys. Res. Commun., 332, 2005, 657-63.
Steward, O. et al., "Compartmentalized synthesis and degradation of proteins in neurons", Neuron, vol. 40, 2003, 347-359.
Steward, O. et al., "Synaptic activation causes the mRNA for the leg Arc to localize selectively near activated postsynaptic sites on dendrites", Neuron, vol. 21, 1998, 741-751.
Strack, R. , "Imaging Bigger is Better for Super-Resolution", Nature Methods, 12(13), Mar. 1, 2015, 169.
Subach, F. V. et al., "Bright monomeric photoactivatable red fluorescent protein for two-color super-resolution sptPALM of live cells", J. Am. Chem. Soc., 132, 2010, 6481-91.
Subach, O. M. et al., "An Enhanced Monomeric Blue Fluorescent Protein with the High Chemical Stability of the Chromophore", PLoS One, 6, 2011, e28674.
Thevenaz, P. et al., "A pyramid approach to subpixel registration based on intensity", IEEE Trans. Image Process., 7, 1998, 27-41.
Tillberg, P. et al., "Protein-Retention Expansion Microscopy of Cells and Tissues Labeled Using Standard Fluorescent Proteins and Antibodies", Nature Biotechnology vol. 34(9), 2016, 987-995.
Van Vliet, et al., "The Biomechanics Toolbox: Experimental Approaches for Living Cells and Biomolecules", Acta Materialia, 51, Aug. 23, 2003, 5881-5905.
Vedaldi, A. et al., Vlfeat. in Proc. Int. Conf. Multimed.—MM '10 1469 (ACM Press, 2010). doi: 10.1145/1873951.1874249.
Wachter, R. M. et al., "Sensitivity of the yellow variant of green fluorescent protein to halides and nitrate", Curr. Biol., 9, 1999, R628-R629.
Wang, F. et al., "RNAscope: A novel in situ RNA analysis platform for formalin-fixed, paraffin-embedded tissues", Journal of Molecular Diagnostics, vol. 14(1), 2012, 22-29.
Wu, C. C. et al., "A method for the comprehensive proteomic analysis of membrane proteins", Nat. Biotechnol., 21, 2003, 532-8.
Xingqi, C. et al., "ATAC-see reveals the accessible genome by transposase-mediated HJ, imaging and sequencing", Nature Methods, vol. 13, No. 12, Dec. 1, 2016, 1013-1020.
Zhang, D. et al., "Dynamic DNA nanotechnology using strand-displacement reactions", Nature Chemistry, vol. 3, 2011, 103-113.
Zimmerman, T. A. et al., "Adapting the stretched sample method from tissue profiling to imaging", Proteomics, 8, 2008, 3809-3815.
New England BioLabs, "Proteinase K", P8102S product datasheet, 1 page, accessed Nov. 17, 2020.
Product information brochure, FLOCRYL™ MBA, SNF Floerger, pp. 1-4, accessed Nov. 17, 2020.
"Crosslinking and Photoactivatable Reagents", Invitrogen, Chapters in "Molecular Probes™ Handbook A Guide to Fluorescent Probes and Labeling Technologies", 11th Edition, 2010, 171-188.
"Proteinase K from Tritirachium album, solution", Serva Electrophoresis, Instruction Manual, Cat. No. 33755, 1 page, publicly available prior to Feb. 1, 2017.
Akhavan, A. et al., "Molecular Epizootiology of Rodent Leishmaniasis in a Hyperendemic Area of Iran", Iranian J Publ Health, vol. 39, No. 1, 2010, 1-7.
Bi, X. et al., "In situ-forming cross-linking hydrogel systems: chemistry and biomedical applications", In: "Emerging Concepts in Analysis and Applications of Hydrogels", INTECH, Aug. 24, 2016, 131-158.
Dilorenzo, F. et al., "Nanostructural Heterogeneity in Polymer Networks and Gels", Polymer Chemistry, vol. 6, 2015, 5515-5528.
Goor, Olga J. et al., "Introduction of anti-fouling coutings at the surface of supramolecular elastomeric materials via post-modification of reactive supramolecular additives", Polymer Chem., vol. 8, No. 34, Jan. 1, 2017, 5228-5238.

(56) References Cited

OTHER PUBLICATIONS

Jiang, Y. et al., "Click hydrogels, microgels and nanogels: emerging platforms for drug delivery and tissue engineering", Biomaterials, vol. 35, No. 18, Jun. 1, 2014, 4969-4985.

Majcher, M. J. et al., "Hydrogel synthesis and design", In: "Cellulose-Based Superabsorbent Hydrogels", Springer International Publishing, Jan. 1, 2018, 1-41.

Meng, H. , "Localization of a Blood Pressure Quantitative Trait Locus (QTL) to a 1.7cM Interval on Rat Chromosome 9", Medical College of Ohio, dissertation, 2002, 1-158.

Orakdogen, N. et al., "Correlation Between Crosslinking Efficiency and Spatial Inhomogeneity in Poly(acrylamide) Hydrogels", Polymer Bulletin, vol. 57, 2006, 631-641.

Oshima, K. et al., "Model Polyelectrolyte Gels Synthesized by End-Linking of Tetra-Arm Polymers with Click Chemistry: Synthesis and Mechanical Properties", Macromolecules, vol. 47, 2014, 7573-7580.

Parang, B. et al., "Myeloid translocation genes differentially regulate colorectal cancer programs", Oncogene, vol. 35, 2016, 6341-6349.

Sakai, T. et al., "Design and Fabrication of a High-Strength Hydrogel with Ideally Homogenous Network Structure from Tetrahedron-Like Macromonomers", Macromolecules, vol. 41, 2008, 5379-5384.

Xu, J. et al., "Bioorthogonally cross-linked hydrogel network with precisely controlled disintegration time over a broad ragne", J. Am. Chem.Soc., vol. 136, No. 11, Mar. 19, 2014, 4105-4108.

Yazici, I. et al., "Spatial Inhomogeneity in Poly(acrylic acid) Hydrogels", Polymer, vol. 46, 2005, 2595-2602.

Zhou, C. et al., "Synthesis and characterization of well-defined PAA-PEG multi-responsive hydrogels by ATRP and click chemistry", RSC ADV., vol. 4, No. 97, Jan. 1, 2014, 54631-54640.

Asano, S. M. et al., "Expansion Microscopy: Protocols for Imaging Proteins and RNA in Cells and Tissues", Current Protocols in Cell Bio., vol. 80, No. 1, Online: DOI: 10.1002/cpcb.56. Retrieved from the Internet: URL:https://onlinelibrary.wiley.com/doi/full-xml/10.1002/cpcb.56> [retrieved on Feb. 26, 2021], Sep. 2, 2018, p. 41.

Yu, C-C et al., "Expansion microscopy of C. elegans", ELIFE, [Online] DOI: 10.7554/eLife.46249. Retrieved from the Internet URL:https://elifesciences.org/articles/46249> [retrieved on Feb. 26, 2021], May 1, 2020, p. 125.

Ferri, A., "Expansion Microscopy: A New Approach to Microscopic Evaluation", Master's thesis, retrieved from https://scholarcommons.sc.edu/etd/6034, 2020.

* cited by examiner

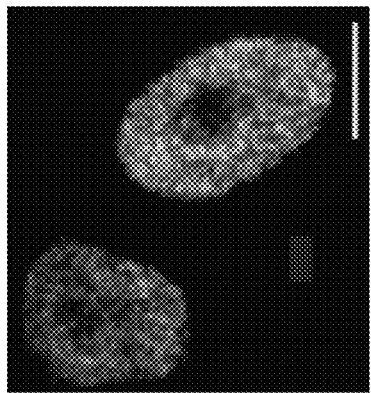
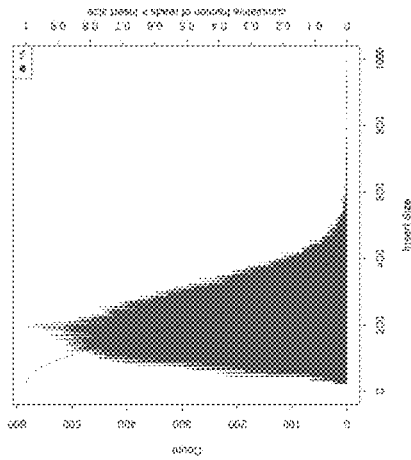
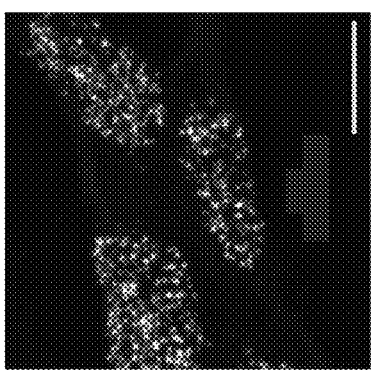
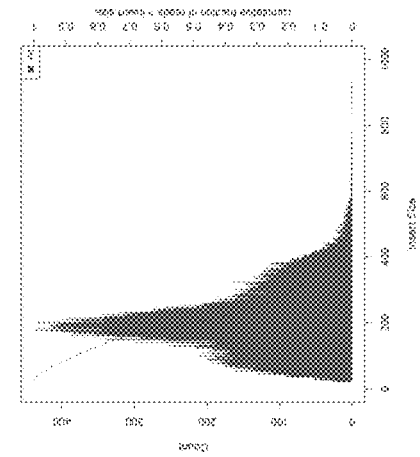
FIG. 9A-9B

IN SITU ATAC SEQUENCING

RELATED APPLICATION

This application claims the benefit of U.S. Provisional Application No. 62/536,628, filed on Jul. 25, 2017. The entire teachings of the above application are incorporated herein by reference.

STATEMENT REGARDING FEDERALLY SPONSORED RESEARCH OR DEVELOPMENT

This invention was made with U.S. government support under Grant Number NYSCF-R-NI10, awarded by NYSCF; Grant Number 5-DPI-NS087724, awarded by National Institute of Health; and Grant Number 5-R01-EY023173, awarded by National Institute of Health. The government has certain rights in this invention.

BACKGROUND

The human body is comprised of a large collection of diverse cell types, each providing a specialized and context-specific function. The establishment and maintenance of a cell's identity is largely driven by chromatin structure, whereby, transcription factors modulate the activity of individual regulatory elements, and chromosomes hierarchically fold to position these regulatory elements to activate or repress the expression of nearby genes.

Recent advances to measure the epigenomes, either by chromatin accessibility (ATAC-seq) or chromatin bound proteins (ChIP-seq), enable the unbiased identification of causative cis and trans regulators driving dynamic cellular phenotypes. Specifically, these existing methods primarily measure i) transcription factors that modulate the activity of regulatory elements (trans) and ii) cis-regulatory elements that drive changes in the expression of nearby genes (cis). While ATAC-Seq and ChIP-Seq have proved instrumental in defining epigenetic variability across cell populations in vitro, these methods fail to resolve either the i) three-dimensional structure or ii) nuclear regulatory complexes that promote cellular variation in situ.

Thus, novel tools are needed to bridge the biological insights of epigenomics methods with the spatial resolution of imaging to understand the structural features governing cellular regulation.

SUMMARY

The present invention provides methods for analyzing polynucleotides such as genomic DNA. In some embodiments, the disclosure provides a method for preparing and amplifying a genomic DNA library in situ in a fixed biological sample. The method comprises treating a fixed biological sample with an insertional enzyme complex to produce tagged fragments of genomic DNA. The method further comprises circularizing the tagged fragments of genomic DNA. The method further comprises amplifying the tagged fragments of genomic DNA.

In some embodiments, the genomic library is constructed from accessible chromatin. In some embodiments, the genomic library is constructed from the whole genome.

The present invention further provides a method for analyzing chromatin in situ in a fixed biological sample. The method comprising (a) preparing a genomic library as described herein; and (b) sequencing all or a portion of the tagged fragments to produce a plurality of sequence reads.

The information obtained from the sequence reads can be used for making an epigenetic map of the genome, or a region thereof, of the fixed sample in situ by mapping the information to the genome, or region thereof.

In some embodiments, the information mapped is selected from one or more of: (i) cleavage sites for the transposase; (ii) the sizes of the fragments produced in step (a); (iii) sequence read length; (iv) the positions of sequence reads of a defined range in length; and (v) sequence read abundance. In some embodiments, the fragments of a defined size range are nucleosome-free fragments.

In some embodiments, the epigenetic map shows one or more of: (i) a profile of chromatin accessibility along the region; (ii) DNA binding protein occupancy for a binding site in the region; (iii) nucleosome-free DNA in the region; (iv) positioning of nucleosomes along the region; and/or (v) chromatin states. In some cases, the method can further comprise measuring global occupancy of a binding site for the DNA binding protein. The DNA binding protein can, for example, be a transcription factor.

In some embodiments, the treating step (a) can comprise incubating the fixed biological sample with the insertional enzyme complex, wherein the incubation results in production of the tagged fragments of genomic DNA.

The term "insertional enzyme complex," as used herein, refers to a complex comprising an insertional enzyme and two adaptor molecules (also referred to as the "molecular tags" or "transposon tags") that are combined with polynucleotides to fragment and add adaptors to the polynucleotides. Such a system is described in a variety of publications, including Caruccio (Methods Mol. Biol. 2011 733: 241-55), US20100120098 and US20160060691, which are incorporated by reference herein.

The insertional enzyme can be a transposase. In some embodiments, the transposase can be derived from Tn5 transposase. In other embodiments, the transposase can be derived from MuA transposase. In further embodiments, the transposase can be derived from Vibhar transposase (e.g. from *Vibrio harveyi*).

In some embodiments, the insertional enzyme can comprise two or more enzymatic moieties wherein each of the enzymatic moieties inserts a common sequence into the accessible chromatin or whole genome. The enzymatic moieties can be linked together. The common sequence can comprise a common barcode. The enzymatic moieties can comprise transposases. The accessible chromatin or whole genome can be fragmented into a plurality of fragments during step (a), wherein the fragments comprising the common barcode are determined to be in proximity in the three-dimensional structure of the polynucleotide.

The present disclosure further provides a diagnostic method, comprising: analyzing chromatin from a patient to produce an epigenetic map; and providing a diagnosis or prognosis based on the epigenetic map.

The present disclosure also provides a method for analyzing the three-dimensional structure of a polynucleotide from a fixed biological sample in situ, comprising: (a) preparing a genomic library as described herein; and (b) using the molecular tags to analyze the three-dimensional structure of the polynucleotide.

In some embodiments, the accessible chromatin can be fragmented into a plurality of fragments during the insertion. The accessibility can be determined by sequencing the fragments and thereby generating a plurality of sequencing reads. The fragments can, for example, be sequenced by a high-throughput sequencing technique. The method can further comprise normalizing the sequencing reads based on the sequence insertion preference of the insertional enzyme. The length of the sequenced reads can also be used to determine a chromatin state annotation.

In some embodiments, the molecular tags can comprise sequencing adaptors, which may further comprise a barcode label. The barcode label can comprise a unique sequence. In other cases, the molecular tags can comprise fluorescence tags.

The insertional enzyme complex can further comprise an affinity tag, which may optionally be an antibody that binds to a transcription factor, a modified nucleosome, and/or a modified nucleic acid. The modified nucleic acid can, for example be a methylated or hydroxymethylated DNA. The affinity tag can also be a single-stranded nucleic acid, which may optionally bind to a target nucleic acid. The insertional enzyme can further comprise a nuclear localization signal.

BRIEF DESCRIPTION OF THE DRAWINGS

Other aspects, advantages and novel features of the invention will become more apparent from the following detailed description of the invention when considered in conjunction with the accompanying drawings wherein:

FIG. 9A and FIG. 9B: Comparison of polyacrylamide-embedded library preps targeting open chromatin and the whole genome. The samples shown in the figure were produced using the protocol described in "Demonstration of in situ genomic library construction", with the following deviations: (i) the '+HCl' sample was treated with 0.1 N HCl for 5 minutes and washed twice with PBS before adaptor insertion, (ii) the RCA primer contained LNA bases and a 5' Acrydite modification, and (iii) the samples were embedded in 5% polyacrylamide before the overnight RCA reaction, rather than after the RCA reaction and visualization. Scale bars are 10 μm.

DETAILED DESCRIPTION

Figures 1A, 1B, 1C:
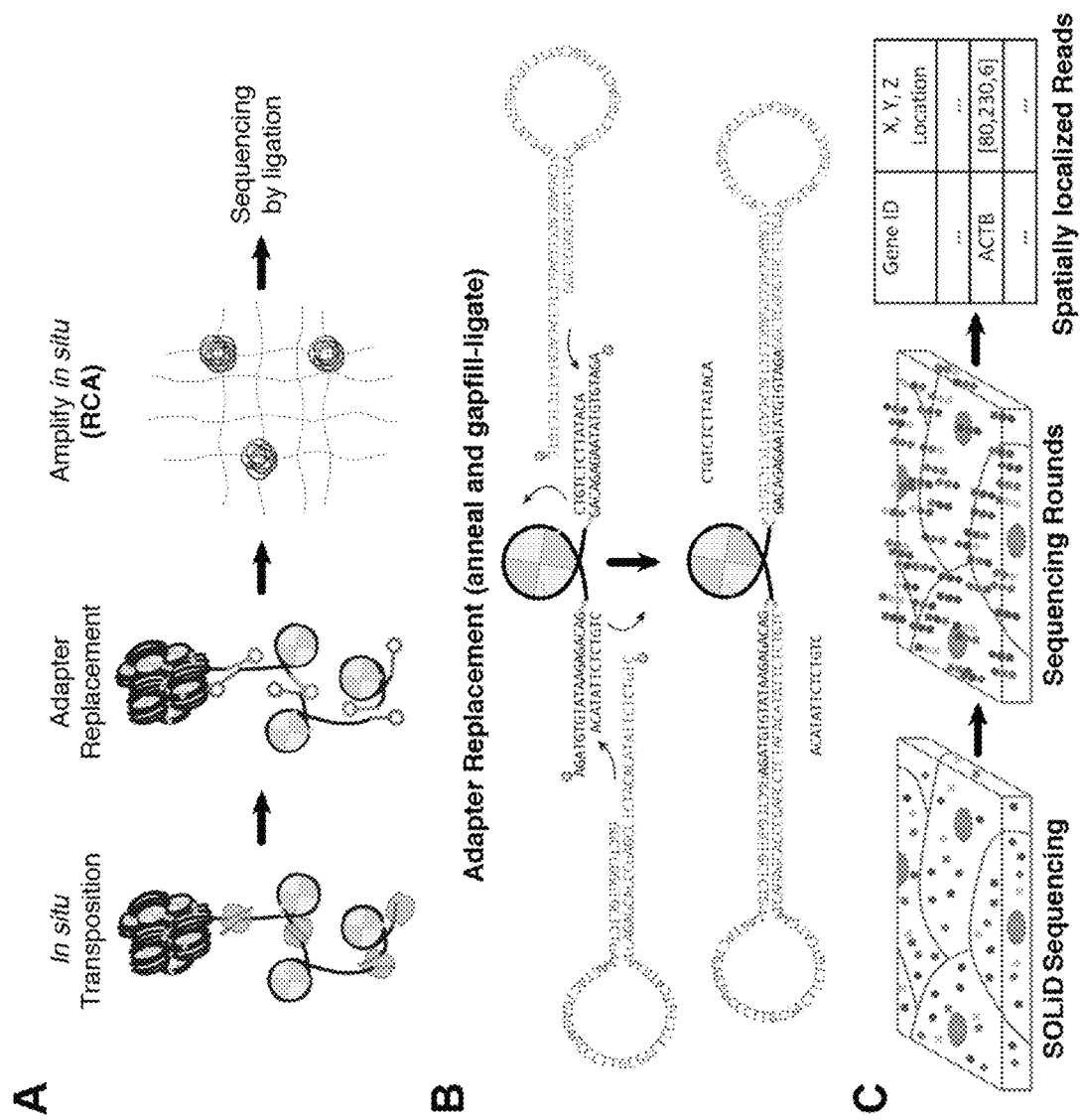
FIG. 1A through FIG. 1C: Schematic of sample preparation workflow for preparing an in situ genome sequencing library. (a) In situ transposition is first performed on fixed cells or tissues, followed by adapter replacement and circularization. Fragments are amplified using, for example, rolling circle amplification (RCA). (b) Schematic representing fragment circularization using ligation of circular adapters to transposed accessible fragments. (c) Schematic of sequencing partial resolved fragments using SOLiD sequencing chemistry.

As used herein and in the appended claims, the singular forms "a", "an", and "the" are defined to mean "one or more" and include the plural unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

This present invention provides for the development of in situ epigenomic tools. A spatially resolved epigenome would provide details of epigenomic changes mediated by intracellular chromosome conformation. In addition, in situ approaches naturally enable combinatorial measurements from the same sample, including direct interrogation into trans effectors and localization with protein complexes or with measures of gene expression. Notably, these methods may also be applied to spatially resolved 'multi-omic' interrogation of complex tissues to provide a spatially resolved '-omic' understanding of the epigenome.

The present invention provides methods for analyzing polynucleotides such as genomic DNA. In some embodiments, the disclosure provides a method for preparing and amplifying a genomic DNA library in situ in a fixed biological sample. The method comprises treating a fixed biological sample with an insertional enzyme complex to produce tagged fragments of genomic DNA. As used herein, in situ generally refers to wherein the tagged fragments are present at their original place (in-situ), i.e., within the cell or tissue, thereby aiding in localizing the sequence within the sample. In some embodiments, the method further comprises circularizing the tagged fragments of genomic DNA. In some embodiments, the method further comprises amplifying the tagged fragments of genomic DNA.

In some embodiments, the genomic library is constructed from accessible chromatin. In some embodiments, the genomic library is constructed from the whole genome.

The term "insertional enzyme complex," as used herein, refers to a complex comprising an insertional enzyme and at least two adaptor molecules (the "transposon tags") that are combined with polynucleotides to fragment and add adaptors to the polynucleotides. In some embodiments, the accessible chromatin or whole genome may be fragmented into a plurality of fragments during the insertion of the molecular tags. In this step, the chromatin or whole genome is tagmented (i.e., cleaved and tagged in the same reaction) using an insertional enzyme such as a transposase that cleaves the genomic DNA in open regions in the chromatin and adds adaptors to both ends of the fragments. Methods for tagmenting isolated genomic DNA are known in the art (see, e.g., Caruccio Methods Mol. Biol. 2011 733: 241-55; Kaper et al, Proc. Natl. Acad. Sci. 2013 110: 5552-7; Marine et al, Appl. Environ. Microbiol. 2011 77: 8071-9, US20100120098 and US20160060691) and are commercially available from Illumina (San Diego, Calif.) and other vendors. Such systems may be readily adapted for use herein. In some cases, the conditions may be adjusted to obtain a desirable level of insertion in the chromatin or whole genome (e.g., an insertion that occurs, on average, every 50 to 200 base pairs in open regions).

The insertional enzyme can be any enzyme capable of inserting a nucleic acid sequence into a polynucleotide. In some cases, the insertional enzyme can insert the nucleic acid sequence into the polynucleotide in a substantially sequence-independent manner. The insertional enzyme can be prokaryotic or eukaryotic. Examples of insertional enzymes include, but are not limited to, transposases, HERMES, and HIV integrase. The transposase can be a Tn transposase (e.g., Tn3, Tn5, Tn7, Tn10, Tn552, Tn903), a MuA transposase, a Vibhar transposase (e.g., from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Te1, THE-1, Tn/O, TnA, Tn3, Tn5, Tn7, Tn10, Tn552, Tn903, Tol1, Tol2, Tn10, Ty1, any prokaryotic transposase, or any transposase related to and/or derived from those listed above. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. In some cases, the insertion can be facilitated and/or triggered by addition of one or more cations. The cations can be divalent cations such as, for example, $Ca^{2+}$, $Mg^{2+}$ and $Mn^{2+}$.

The adaptor molecules can comprise additional sequences that can be used for amplification, detection and/or sequencing. Such additional sequences can include, but are not limited to, sequencing adaptors, primer binding sites, locked nucleic acids (LNAs), zip nucleic acids (ZNAs), RNAs, affinity reactive molecules (e.g., biotin, dig), self-complementary molecules, phosphorothioate modifications, DNA tags, barcodes, and azide or alkyne groups. In some embodiments, the sequencing adaptors can further comprise a barcode label. Further, the barcode labels can comprise a unique sequence. The unique sequences can be used to identify the individual insertion events. Any of the tags can further comprise fluorescence tags (e.g., fluorescein, rhodamine, Cy3, Cy5, thiazole orange, etc.).

In some embodiments, the adaptor molecules can comprise unmodified DNA oligonucleotides. Examples of such unmodified DNA oligonucleotides include, but are not limited to, oligonucleotides consisting of the 19 basepair mosaic end Tn5 transposase recognition sequence, oligonucleotides which contain the recognition sequence as a subsequence as well as containing an additional sequence as a subsequence (e.g., Illumina Read 1 or Read 2 or any user-defined sequence). In some embodiments, the adaptor molecules can comprise modified DNA oligonucleotides. As used herein, "modified DNA oligonucleotides" refer to oligonucleotides which contain a chemical modification on the 5' end, the 3' end, or internally, and/or oligonucleotides that incorporate non-standard DNA bases (e.g., uracil, xenonucleic acids). Examples of such modified DNA oligonucleotides include, but are not limited to, 5' or 3' phosphorylation, 5' acrydite modification, internal methacrylate functionalized uracil.

In some embodiments, the insertional enzyme can comprise two or more enzymatic moieties wherein each of the enzymatic moieties inserts a common sequence into the accessible chromatin or whole genome. The enzymatic moieties can be linked together. The common sequence can comprise a common barcode. The enzymatic moieties can comprise transposases. The accessible chromatin or whole genome can be fragmented into a plurality of fragments during step (a), wherein the fragments comprising the common barcode are determined to be in proximity in the three-dimensional structure of the polynucleotide.

In some embodiments, the tagged fragments of genomic DNA can be circularized. Circularization of the tagged fragments of genomic DNA can be accomplished by any suitable method known to one skilled in the art including, but not limited to, oligonucleotide displacement, hairpin hybridization, gap repair, and ligation. For example, the biological sample is exposed to a ligase and upon recognition of and hybridization to the tagged fragments of genomic DNA the 5' end and the 3' end of tagged fragments of genomic DNA are ligated to each other through the action of the ligase, forming a circular structure. In other words, the 5' end and the 3' end of a tagged fragment are brought into juxtaposition, forming a circle, which allows the ends to be covalently joined by the action of a ligase. As the tagged fragments comprise genomic DNA, the ligation products are in the form of a circle of double-stranded genomic DNA.

Ligation can be accomplished either enzymatically or chemically. "Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between 5' carbon of a terminal nucleotide of the tagged fragment of genomic DNA with the 3' carbon of the tagged fragment of genomic DNA.

A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) Nucl. Acids Res. 27:875; Higgins et al., Meth. in Enzymol. (1979) 68:50; Engler et al. (1982) The Enzymes, 15:3 (1982); and Namsaraev, U.S. Patent Pub. 2004/0110213.

Chemical ligation methods are disclosed in Ferris et al., Nucleosides & Nucleotides, 8: 407-414 (1989) and Shabarova et al., Nucleic Acids research, 19: 4247-4251 (1991). Enzymatic ligation utilizes a ligase. Many ligases are known to those of skill in the art as referenced in Lehman, Science, 186: 790-797 (1974); Engler et al., DNA ligases, pages 3-30 in Boyer, editor, The Enzymes, Vol. 15B (Academic Press, New York, 1982); and the like. Exemplary ligases include SplintR ligase, T4 DNA ligase, T7 DNA ligase, E. coli DNA ligase, Taq ligase, Pfu ligase and the like. Certain protocols for using ligases are disclosed by the manufacturer and also in Sambrook, Molecular Cloning: A Laboratory manual, 2.sup.nd Edition (Cold Spring Harbor Laboratory, New York, 1989); Barany, PCR Methods and Applications, 1:5-16 (1991); Marsh et al., Strategies, 5:73-76 (1992). In one embodiment, the ligase may be derived from algal viruses such as the Chlorella virus, for example, PBCV-1 ligase, also known as SplintR ligase, as described US Patent Publication No. 2014/0179539, incorporated herein by reference in its entirety.

In some embodiments, the method further comprises amplifying the tagged fragments of genomic DNA. The expression "amplification" or "amplifying" refers to a process by which extra or multiple copies of a particular polynucleotide are formed. The term "amplification product" refers to the nucleic acids, which are produced from the amplifying process as defined herein.

Amplification includes methods generally known to one skilled in the art such as, but not limited to, PCR, ligation amplification (or ligase chain reaction, LCR), real time (rtPCR) or quantitative PCR (qPCR), rolling circle amplification (RCA), and other amplification methods. These methods are generally known. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In one embodiment, the ligation product is amplified using PCR. In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e., each primer is specifically designed to be complementary to each strand of the genomic locus to be amplified. In one embodiment, the tagged fragments of genomic DNA are amplified using qPCR. Quantitative polymerase chain reaction is used to simultaneously detect a specific DNA sequence in a sample and determine the actual copy number of this sequence relative to a standard. In one embodiment, the tagged fragments of genomic DNA are amplified using rtPCR. In real-time PCR, the DNA copy number can be established after each cycle of amplification. By using a fluorescent reporter in the reaction, it is possible to measure DNA generation.

In one embodiment, the tagged fragments of genomic DNA are amplified using Rolling circle amplification (RCA). RCA describes a process of unidirectional nucleic acid replication that can rapidly synthesize multiple copies of circular molecules of DNA or RNA.

In some embodiments, the tagged fragments can be sequenced to generate a plurality of sequencing reads. This may be used to determine the accessibility of the polynucleotide at any given site. The fragments may be sequenced using a high-throughput sequencing technique. In some cases, the sequencing reads can be normalized based on the sequence insertion preference of the insertional enzyme. The length of the sequenced reads can be used to determine a chromatin state annotation.

Additionally, the insertional enzyme complex can further comprise an affinity tag. In some cases, the affinity tag can be an antibody. The antibody can bind to, for example, a transcription factor, a modified nucleosome or a modified nucleic acid. Examples of modified nucleic acids include, but are not limited to, methylated or hydroxymethylated DNA. In other cases, the affinity tag can be a single-stranded nucleic acid (e.g., ssDNA, ssRNA). In some examples, the single-stranded nucleic acid can bind to a target nucleic acid. In further cases, the insertional enzyme complex can further comprise a nuclear localization signal.

In some embodiments, the fixed biological sample can be permeabilized to allow access for the insertional enzyme. The permeabilization can be performed in a way to minimally perturb the nuclei in the sample. In some instances, the sample can be permeabilized using a permeabilization agent. Examples of permeabilization agents include, but are not limited to, NP40, digitonin, tween, streptolysin, and cationic lipids. In other instances, the sample can be permeabilized using hypotonic shock and/or ultrasonication. In other cases, the insertional enzyme can be highly charged, which may allow it to permeabilize through cell membranes.

The term "fixed biological sample" is used herein in a broad sense and is intended to include sources that contain nucleic acids and can be fixed. Exemplary biological samples include, but are not limited to tissues, including but not limited to, liver, spleen, kidney, lung, intestine, thymus, colon, tonsil, testis, skin, brain, heart, muscle and pancreas tissue. Other exemplary biological samples include, but are not limited to, biopsies, bone marrow samples, organ samples, skin fragments and organisms. Materials obtained from clinical or forensic settings are also within the intended meaning of the term biological sample. Preferably, the sample is derived from a human, animal or plant. Preferably, the biological sample is a tissue sample, preferably an organ tissue sample. Preferably, samples are human. The sample can be obtained, for example, from autopsy, biopsy or from surgery. It can be a solid tissue such as, for example, parenchyme, connective or fatty tissue, heart or skeletal muscle, smooth muscle, skin, brain, nerve, kidney, liver, spleen, breast, carcinoma (e.g., bowel, nasopharynx, breast, lung, stomach etc.), cartilage, lymphoma, meningioma, placenta, prostate, thymus, tonsil, umbilical cord or uterus. The tissue can be a tumor (benign or malignant), cancerous or precancerous tissue. The sample can be obtained from an animal or human subject affected by disease or other pathology or suspected of same (normal or diseased), or considered normal or healthy. As used herein, the term "fixed biological sample", explicitly excludes cell-free samples, for example cell extracts, wherein cytoplasmic and/or nuclear components from cells are isolated.

Fixation of the biological sample can be effected with fixatives known to the person skilled in the art. In one embodiment, the fixative, includes but is not limited to, acids, alcohols, ketones or other organic substances, such as, glutaraldehyde, formaldehyde or paraformaldehyde. Examples of fixatives and uses thereof may be found in Sambrook et al. (2000); Maniatis et al. (1989). Preferably, the used fixation also preserves DNA and RNA. According to one embodiment of the process according to the invention, a formaldehyde-fixed, paraffin-embedded biological sample (FFPE sample) is used. Other fixatives and fixation methods for providing a fixed biological sample are known in the prior art. For example, the biological sample can be fresh froze, wherein alcohol based fixed samples can be used. In one embodiment, the fixed tissue may or may not be embedded in a non-reactive substance such as paraffin. In one embodiment, the fixed tissue may or may not be embedded in an unswellable hydrogel. Embedding materials include, but are not limited to, paraffin, mineral oil, non-water soluble waxes, celloidin, polyethylene glycols, polyvinyl alcohol, agar, gelatine, nitrocelluloses, methacrylate resins, epoxy resins or other plastic media. Thereby, one can produce tissue sections of the biological material suitable for histological examinations.

Alternatively or additionally, the fixed biological sample can be an expandable biological sample. By "expandable sample" it is generally meant that the sample is able to be physically expanded, or enlarged, relative to the sample prior to be exposed to the method(s) described herein. In one embodiment, fixation of the biological sample can be effected by embedding the sample in a swellable material that has been perfused throughout the sample as described by Chen et al. (Chen et al., *Science*, 347, 543 (2015) and U.S. Patent Publication Nos. US 2016-0116384-A1; US 2016-0305856-A1; US 2016-0304952-A1; and U.S. patent application Ser. Nos. 15/229,539 and 15/229,545 incorporated herein by reference in their entirety).

In one embodiment, an expandable biological sample can also be prepared by contacting the sample with a bi-functional linker, wherein the bi-functional linker comprises a binding moiety which binds to target nucleic acids in the sample and a polymerization moiety; permeating the sample with a composition comprising precursors of a swellable material; and initiating polymerization to form a swellable material. During or after polymerization, the swellable material can be anchored or cross-linked (e.g., covalently cross-linked) to the sample via the polymerization moiety to form a sample-swellable material complex. The sample-swellable material complex is optionally treated with protease to homogenize the mechanical characteristics of the sample. The sample-swellable material complex can then be treated by dialysis in a solvent or liquid, such as in water, resulting in isotropic physical expansion of the sample. In this manner, the fixed biological sample is physically "enlarged", or "expanded", as compared to the biological sample before swelling.

In some embodiments, the sample is embedded in a swellable or unswellable material following permeabilization of the fixed biological sample. Embedding the sample at this stage limits the diffusion of unfixed fragments.

In one embodiment, the polymerization moiety comprises reactive groups to functional groups (e.g., primary amines or sulfhydryls) on biomolecules within the sample. The bi-functional linker may be used to chemically modify the amine group of biomolecules with a swellable polymer functional group, which enables target nucleic acids within the sample to be directly anchored to, or incorporated into, the swellable polymer.

In one embodiment, the bifunctional linker is a hetero-bifunctional linker. Hetero-bifunctional linkers possess different reactive groups at either end of a spacer arm, i.e., atoms, spacers or linkers separating the reactive groups. These reagents not only allow for single-step conjugation of molecules that have the respective target functional group, but they also allow for sequential (two-steps) conjugations that minimize undesirable polymerization or self-conjugation.

The polymerization moiety may be a physical, biological, or chemical moiety that attaches or crosslinks the sample to the swellable material. This may be accomplished by cross-linking the polymerization moiety with the swellable material, such as during or after the polymerization, i.e., in situ formation of the swellable material. The polymerization moiety may include, but is not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives. The polymerizable moiety may be, for example, an acrylamide modified moiety that may be covalently fixed within a swellable material.

In one embodiment, the bi-functional linker may be a small molecule linker or a nucleic acid adaptor.

As used herein, a "nucleic acid adaptor" is a nucleic acid sequence having a binding moiety capable of attaching to a target nucleic acid and a polymerization moiety (e.g., anchor) capable of attaching to the swellable material. Attaching the nucleic acid adaptor to a target nucleic acid may be accomplished by hybridization or by ligation in situ. For example, DNA adaptors may be ligated to the 3' ends of the RNAs in the sample with RNA ligases, such as T4 RNA ligase, or may be attached via a chemical linker such as a reactive amine group capable of reacting with target nucleic acid. Acrylamide modified oligonucleotide primers may be covalently fixed within a swellable material such as a polyacrylate gel. As used herein, the term "acrylamide modified" in reference to an oligonucleotide means that the oligonucleotide has an acrylamide moiety attached to the 5' end of the molecule.

As used herein, a "small molecule linker" is a small molecule having a binding moiety capable of attaching to a target nucleic acid and a polymerization moiety (e.g., anchor) capable of attaching to the swellable material. Attaching the small molecule linker to the target nucleic acid may be accomplished by hybridization or by a chemical reactive group capable of covalently binding the target nucleic acid. For example, Label-IT® Amine (MirusBio) is a small molecule with alkylating group that primarily reacts to the N7 of guanine, thereby allowing covalent binding of RNA and DNA. The small molecule linker may be, for example, acrylamide modified and therefore may be covalently fixed within a swellable material. As used herein, the term "acrylamide modified" in reference to a small molecule linker means that the small molecule linker has an acrylamide moiety.

As used herein, the term "attach" or "attached" refers to both covalent interactions and noncovalent interactions. In certain embodiments of the invention, covalent attachment may be used, but generally all that is required is that the bi-functional linker remain attached to the target nucleic acid under conditions for nucleic acid amplification and/or sequencing. Oligonucleotide adaptors may be attached such that a 3' end is available for enzymatic extension and at least a portion of the sequence is capable of hybridizing to a complementary sequence. Attachment can occur via hybridization to the target nucleic acid, in which case the attached oligonucleotide may be in the 3'-5' orientation. Alternatively, attachment can occur by means other than base-pairing hybridization, such as the covalent attachment set forth above. The term "attach" may be used interchangeably herein with the terms, "anchor(ed)", affix(ed), link(ed) and immobilize(d).

As used herein, the term "swellable material" generally refers to a material that expands when contacted with a liquid, such as water or other solvent. Preferably, the swellable material uniformly expands in 3 dimensions, i.e., isotropically. Additionally or alternatively, the material is transparent such that, upon expansion, light can pass through the sample. The swellable material may be a swellable polymer or hydrogel.

The swellable material may be formed in situ from precursors thereof. By "precursors of the polymer" it is meant monomers that can be "polymerized" through a crosslinking mechanism, to form a three-dimensional (3D) polymer network. One or more polymerizable materials, such as monomers or oligomers can be used. For example, such as monomers may be selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N, N-alkylene bisacrylamides). Precursors can also comprise polymerization initiators and crosslinkers. The precursors of a swellable material may comprise at least one polyelectrolyte monomer and a covalent crosslinker.

The swellable material may be formed in situ by chemically crosslinking water soluble oligomers or polymers. Thus, the invention envisions adding precursors of the swellable material to the sample and rendering the precursors swellable in situ. The sample may be permeated (such as, perfusing, infusing, soaking, adding or other intermixing) with the precursors of the swellable material, wherein the sample is saturated with precursors of the swellable material, which flow between and around biomolecules throughout the specimen. Polymerizing and/or crosslinking the monomers or precursors is initiated to form the swellable material or polymer in situ. In this manner the biological sample is embedded in the swellable material.

Following permeating the specimen, the swellable polymer precursors are polymerized, i.e., covalently or physically crosslinked, to form a polymer network. The polymer network is formed within and throughout the specimen. In this manner, the biological specimen is saturated with the swellable material, which flow between and around biomolecules throughout the specimen.

Polymerization may be by any method including, but not limited to, thermal crosslinking, chemical crosslinking, physical crosslinking, ionic crosslinking, photo-crosslinking, irradiative crosslinking (e.g., x-ray, electron beam), and the like, and may be selected based on the type of hydrogel used and knowledge in the art. In one embodiment, the polymer is a hydrogel. Once polymerized, a polymer-embedded biological specimen is formed.

The swellable polymer may be a polyacrylate or polyacrylamide and copolymers or crosslinked copolymers thereof. For example, if the biological sample is to be embedded in sodium polyacrylate, a solution comprising the monomers sodium acrylate and acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), are perfused throughout the sample.

In one embodiment, the swellable material is a hydrogel. In one embodiment, the hydrogel is a polyelectrolyte hydrogel. In one embodiment, the polyelectrolyte is a polyacrylate.

In one embodiment, the swellable material is a DMAA-TF polymer. The sample with a composition comprising acrylamide, dimethylacrylamide, and sodium acrylate linear monomers at a concentration of about 20 about 50 wt % of which sodium acrylate comprises about 10 to about 25 mol %, about 0.1 to about 1.0 mol % polymerization initiator, and about 0.001 to about 0.01 wt % polymerization accelerator; and polymerizing the composition within the sample to form a polymer. In one embodiment, the composition may further comprise about 0.005 to about 0.02 wt % polymerization inhibitor.

In some embodiments, the concentration of linear monomers in the composition is about 30 to about 40 wt %. In embodiments, the concentration of linear monomers in the composition is about 35 wt %. In embodiments, the concentration of linear monomers in the composition is about 33 wt %.

In embodiments, the concentration of sodium acrylate is about 15 to about 20 mol % of the linear monomer concentration. In embodiments, the concentration of sodium acrylate is about 15 mol % of the linear monomer concentration. In embodiments, the concentration of sodium acrylate is about 20 mol % of the linear monomer concentration.

As used herein, polymerization initiator generally refers to reagents that react with a monomer to form an intermediate compound capable of linking successively with a large number of other monomers into a polymeric compound. Polymerization initiators include, but are not limited to, potassium persulfate (KPS), ammonium persulfate, di-tert-butyl peroxide (DTBP), benzoyl peroxide (BPO), methyl ethyl ketone peroxide (MEKP), acetone peroxide, VA-044 (2,2'-azobis[2-(2-imidazolin-2-yl)propane]dihydrochloride), azobisisobutyronitrile (AIBN), 1,1'-azobis(cyclohexanecarbonitrile) (ACHN), carbon halides. In embodiments, the polymerization initiator is potassium persulfate (KPS). In embodiments, the composition comprises about 0.4 mol % polymerization initiator.

As used herein, polymerization accelerator generally refers to reagents that stabilize the polymerization initiator and catalyze the polymerization process. Polymerization accelerators include, but are not limited to, N,N,N',N'-Tetramethylethylenediamine (TEMED), sodium bisulfate. In embodiments, the polymerization accelerator is TEMED In embodiments, the composition comprises about 0.005 wt % polymerization accelerator.

As used herein, polymerization inhibitor generally refers to compounds which can trap free radicals and are used to inhibit radical polymerization. Such inhibitors may prevent polymerization initiation caused by, for example, light, heat or air. Polymerization Inhibitors include reagents that reacts very rapidly with the initiating radicals to almost completely suppress the polymerization reaction, that is, the inhibitor has to be completely consumed before the reaction rate assumes its normal value as well as reagents that react only mildy with the initiating free radicals so that some inititators escape and are able to initiate polymerization reduce the rate of polymerization, that is, the rate of reaction steadily increases as the retarder is consumed. The use of a polymerization inhibitor inhibits the formation of radicals allowing the composition comprising the precursors of the polymer to fully fill the cell or tissue sample. Polymerization inhibitors include, but are not limited to, 4-Hydroxy-TEMPO (4HT), 4-oxo-TEMPO, TEMPO, 4-Hydroxy-TEMPO-$d_{17}$, 4-amino-TEMPO, free radical, 4-tert-Butylcatechol, 4-tert-Butylpyrocatechol, tert-Butylhydroquinone, 1,4-Benzoquinone, 6-tert-Butyl-2,4-xylenol, 2,6-Di-tert-butyl-p-cresol, 2,6-Di-tert-butylphenol, 1,1-Diphenyl-2-picrylhydrazyl Free Radical, Hydroquinone, 4-Methoxyphenol, Phenothiazine. In embodiments, the polymerization inhibitor is 4HT. In embodiments, the composition comprises about 0.01 wt % polymerization inhibitor.

The fixed, expandable biological sample may be expanded. Expanding the sample may be accomplished by adding an aqueous solvent or liquid to cause the sample-swellable material complex to swell, thereby physically expanding the complex.

The expandable biological sample, can, optionally, be treated with a detergent prior to being contacted with the precursors of the swellable material. The use of a detergent can improve the wettability of the sample or disrupt the sample to allow the precursors of the swellable monomer to permeate throughout sample.

After the sample has been anchored to the swellable material, the sample is, optionally, subjected to a disruption of the endogenous biological molecules leaving the target nucleic acids intact and anchored to the swellable material. In this way, the mechanical properties of the sample-swellable material complex are rendered more spatially uniform, allowing isotropic expansion with minimal artifacts.

As used herein, the "disruption of the endogenous physical structure of the sample" or the term "disruption of the endogenous biological molecules" of the biological sample generally refers to the mechanical, physical, chemical, biochemical or, preferably, enzymatic digestion, disruption or break up of the sample so that it will not resist expansion. A protease enzyme may be used to homogenize the sample-swellable material complex. The disruption should not impact the structure of the swellable material but disrupt the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample. The disruption of the physical structure of the sample may be protein digestion of the proteins contained in the biological sample.

In one embodiment, a non-specific protease is used to homogenize the sample-polymer complex. In one embodiment, the method may further comprise the step of incubating the sample with a non-specific protease in a buffer comprising a metal ion chelator, a non-ionic surfactant, and a monovalent salt. In one embodiment, the method comprises incubating the sample with 1-100 U/ml of a non-specific protease in a buffer having a pH between about 4 and about 12, the buffer comprising about 5 mM to about 100 mM metal ion chelator, about 0.1% to about 1.0% non-ionic surfactant, and about 0.05 M to about 1 M monovalent salt. In one embodiment, the sample is incubated for about 0.5 to about 3 hours at about 50° C. to about 70° C. In one embodiment, the sample is incubated in the buffer until the sample is completely digested.

In one embodiment, the non-specific protease is in a buffer having a pH from about 4 to about 12. Any suitable buffer agent can be used including, but not limited to, Tris, citrate, phosphate, bicarbonate, MOPS, borate, TAPS, bicine, Tricine, HEPES, TES, and MES.

Non-specific proteases are well known to those of skill in the art. Non-specific proteases include, but are not limited to, proteinase K, Subtilisin, Pepsin, Thermolysin, and Elastase. In one embodiment the buffer comprises about 1 U/ml to about 100 U/ml of a non-specific protease. In one embodiment the buffer comprises about 1 U/ml to about 50 U/ml of a non-specific protease. In one embodiment the buffer comprises about 1 U/ml to about 25 U/ml of a non-specific protease. In one embodiment the buffer comprises about 1 U/ml to about 10 U/ml of a non-specific protease.

Chelating agents are well known to those of skill in the art. Chelating agents include, but are not limited to, EDTA, EGTA, EDDHA, EDDS, BAPTA and DOTA. In one embodiment the buffer comprises about 5 mM to about 100 mM of a metal ion chelator. In one embodiment the buffer comprises about 5 mM to about 75 mM of a metal ion chelator. In one embodiment the buffer comprises about 5 mM to about 50 mM of a metal ion chelator.

Nonionic surfactant are well known to those of skill in the art. Nonionic surfactants include, but are not limited to, Triton X-100, Tween 20, Tween 80, Sorbitan, Polysorbate 20, Polysorbate 80, PEG, Decyl glucoside, Decyl polyglucose and cocamide DEA. In one embodiment the buffer comprises about 0.1% to about 1.0% nonionic surfactant. In one embodiment the buffer comprises about 0.1% to about 0.75% nonionic surfactant. In one embodiment the buffer comprises about 0.1% to about 0.5% nonionic surfactant. In one embodiment the buffer comprises about 0.1% to about 0.3% nonionic surfactant.

Monovalent cation salts are well known to those of skill in the art. Monovalent cation salts contain cations that include, but are not limited to, $Na^+$, $K^+$, ammonium, and $Cs^-$. In one embodiment, the buffer comprises about 0.05 M to about 1.0 M monovalent salt. In one embodiment, the buffer comprises about 0.05 M to about 1.0 M monovalent salt. In one embodiment, the buffer comprises about 0.75 M to about 1.0 M monovalent salt. In one embodiment, the buffer comprises about 0.1 M to about 1.0 M monovalent salt. In one embodiment, the buffer comprises about 0.1 M to about 0.7 M monovalent salt. In one embodiment, the buffer comprises about 0.05 M to about 0.8 M monovalent salt.

It is preferable that the disruption does not impact the structure of the polymer but disrupts the structure of the sample. Thus, the sample disruption should be substantially inert to the polymer. The degree of digestion can be sufficient to compromise the integrity of the mechanical structure of the sample or it can be complete to the extent that the sample-polymer complex is rendered substantially free of the sample.

The expandable cell or tissue sample can be expanded by contacting the sample-polymer complex with a solvent or liquid to cause the polymer to swell. By expanding, or swelling, the expandable sample it is generally meant that the sample is physically expanded, or enlarged, relative to the sample prior to be exposed to the method(s) described herein. The swelling of the polymer results in the sample itself expanding (e.g., becoming larger). This is because the polymer is embedded throughout the sample, therefore, by binding, e.g., anchoring, biomolecules to the polymer network and swelling, or expanding, the polymer network, the biomolecules are thereby moved apart. In one embodiment, the swellable polymer expands (swells) isotropically. As the biomolecules are anchored to the polymer network isotropic expansion of the polymer network retains the spatial orientation of the biomolecules resulting in an expanded, or enlarged, sample.

The expanded sample can then be subjected to microscopic analysis. By "microscopic analysis" it is meant the analysis of a sample using any technique that provides for the visualization of aspects of a sample that cannot be seen with the unaided eye, i.e., that are not within the resolution range of the normal eye.

The expanded sample-polymer complex can be imaged on any optical microscope, allowing effective imaging of features below the classical diffraction limit. Since the resultant expanded sample can be transparent, custom microscopes capable of large volume, wide field of view, 3D scanning may also be used in conjunction with the expanded sample.

Because biomolecules of the sample are anchored to a polymer that physically supports the ultrastructure of the sample, cellular components (e.g. lipids) that normally provide structural support but that hinder visualization of subcellular proteins and molecules may be removed while preserving the 3-dimensional architecture of the cells and tissue. This removal renders the interior of sample substantially permeable to light and/or macromolecules, allowing the interior of the sample, e.g. cells and subcellular structures, to be microscopically visualized without time-consuming and disruptive sectioning.

Additionally, the sample can be iteratively stained, unstained, and re-stained with other reagents for comprehensive analysis.

By "biomolecules" it is generally meant, but not limited to, proteins, lipids, steroids, nucleic acids, and sub-cellular structures within a tissue or cell.

By "macromolecules" is meant proteins, nucleic acids, or small molecules that target biomolecules within the sample. These macromolecules are used to detect biomolecules within the sample and/or anchor the biolmolecules to the swellable polymer. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

As an example, the sample may be contacted with one or more polypeptide macromolecules, e.g. antibodies, labeled peptides, and the like, that are specific for and will bind to particular cellular biomolecules for either direct or indirect labeling by color or immunofluorescence. By immunofluorescence it is meant a technique that uses the highly specific binding of an antibody to its antigen or binding partner in order to label specific proteins or other molecules within the cell. A sample is treated with a primary antibody specific for the biomolecule of interest. A fluorophore can be directly conjugated to the primary antibody or peptide. Alternatively a secondary antibody, conjugated to a detection moiety or fluorophore, which binds specifically to the first antibody can be used. Peptides that are specific for a target cellular biomolecule and that are conjugated to a fluorophore or other detection moiety may also be employed.

Another example of a class of agents that may be provided as macromolecules is nucleic acids. For example, a sample may be contacted with an antisense RNA that is complementary to and specifically hybridizes to a transcript of a gene of interest, e.g., to study gene expression in cells of the sample. As another example, a sample may be contacted with a DNA that is complementary to and specifically hybridizes to genomic material of interest, e.g., to study genetic mutations, e.g., loss of heterozygosity, gene duplication, chromosomal inversions, and the like. The hybridizing RNA or DNA is conjugated to detection moieties, i.e. agents that may be either directly or indirectly visualized microscopically. Examples of in situ hybridization techniques may be found at, for example, Harris and Wilkinson. In situ hybridization: Application to developmental biology and medicine, Cambridge University Press 1990; and Fluorescence In Situ Hybridization (FISH) Application Guide. Liehr, T, ed., Springer-Verlag, Berlin Heidelberg 1990.

In some embodiments, the sample is embedded in a swellable or unswellable hydrogel following transposition. Embedding the sample at this stage limits the diffusion of the tagged fragments of genomic DNA. Additionally, embedding the sample at this stage allows for embedding the tagged fragments of genomic DNA in the hydrogel as well if the adaptors molecules comprise a polymerizable group.

In some embodiments, the sample is embedded in a swellable or unswellable hydrogel following circularization. Embedding the sample at this stage allows for embedding the tagged fragments of genomic DNA in the hydrogel as well if the hairpin has a polymerizable group.

In some embodiments, the sample is embedded in a swellable or unswellable hydrogel following amplification. Embedding the sample at this stage allows for embedding of the amplicons in the hydrogel as well to permit digestion and sample clearing from the fixed biological sample.

In some embodiments, the enlarged sample can be re-embedded in a non-swellable material. "Re-embedding" comprises permeating (such as, perfusing, infusing, soaking, adding or other intermixing) the sample with the non-swellable material, preferably by adding precursors thereof. Alternatively or additionally, embedding the sample in a non-swellable material comprises permeating one or more monomers or other precursors throughout the sample and polymerizing and/or crosslinking the monomers or precursors to form the non-swellable material or polymer. In this manner the first enlarged sample, for example, is embedded in the non-swellable material. Embedding the expanded sample in a non-swellable material prevents conformational changes during sequencing despite salt concentration variation. The non-swellable material can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

The expandable biological sample can be expanded prior to or after the treating step, amplification step or after the optional ligation step. In other words, the step of expanding the biological sample can be independently performed before or after the treating step, amplification step or ligation step. In view of the flexibility in the order of the performing each step, the article "a" is used to describe the biological sample in each step to ensure that, in each instance, the biological sample is not necessarily the product produced by the preceding step. For example, the product of step (a) can be the result of incubating a biological sample as directly obtained from a subject with an insertional complex. Alternatively, the product of step (a) can be the result of incubating a fixed biological sample with an insertional complex.

In some embodiments, the fixed biological sample is subjected to passivation. As used herein the term "passivation" refers to the process for rendering the sample less reactive with the components contained within the fixative such as by functionalizing the fixative with chemical reagents to neutralize charges within. For example, the carboxylic groups of acrylate, which may be used in the swellable gel, can inhibit downstream enzymatic reactions. Treating the swellable gel composed of acrylate with 1-Ethyl-3-(3-dimethylaminopropyl)carbodiimide (EDC) and N-Hydroxysuccinimide (NHS) allows primary amines to covalently bind the carboxylic groups to form charge neutral amides and passivate the swellable gel.

The biological sample may be labeled or tagged with a detectable label. Typically, the label or tag will bind chemically (e.g., covalently, hydrogen bonding or ionic bonding) to the sample, or a component thereof. The detectable label can be selective for a specific target (e.g., a biomarker or class of molecule), as can be accomplished with an antibody or other target specific binder. The detectable label preferably comprises a visible component, as is typical of a dye or fluorescent molecule; however, any signaling means used by the label is also contemplated. A fluorescently labeled biological sample, for example, is a biological sample labeled through techniques such as, but not limited to, immunofluorescence, immunohistochemical or immunocytochemical staining to assist in analysis. Thus, the detectable label may be chemically attached to the biological sample, or a targeted component thereof. The detectable label may be an antibody and/or fluorescent dye wherein the antibody and/or fluorescent dye further comprises a physical, biological, or chemical anchor or moiety that attaches or crosslinks the sample to the composition, hydrogel or other swellable material. The detectable label may be attached to the bifunctional linker. The detectable label may be attached to the nucleic acid adaptor or the small molecule linker. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides Additionally, a polynucleotide can be native to the sample (for example, present in the sample at the time the sample is obtained from the original organism). Alternatively, a polynucleotide can be artificial or synthetic, such as when the polynucleotide is added to the sample to cause hybridization to a target RNA. The term "polynucleotide" is intended to include polynucleotides comprising naturally occurring nucleotides and/or non-naturally occurring nucleotides. Non-naturally occurring nucleotides can include chemical modifications of natural nucleotides. In this case, it is preferred that the synthetic polynucleotides can hybridize to the tagged genomic fragments.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of includes determining the amount of something present, as well as determining whether it is present or absent.

Through suitable design of a probe sequence outside the tagged portion of the genomic DNA, detection may be performed through various methods. One example is loop-mediated isothermal amplification (LAMP), wherein probes are designed to form LAMP target structures upon ligation (Notomi, et al., *Nucleic Acids Res.,* 28(12): e63 (2000)). Presence of target RNA is then detected via LAMP amplification, enabling advantages such as isothermal reaction conditions, rapid detection, and implementation in field or point-of-care diagnostics. Upon successful ligation, detection of amplification of target nucleic acid via may be performed with traditional qPCR dyes and probes as described above, or with additional methodologies: turbidity detection of precipitated magnesium pyrophosphate (Mori, et. al., *Biochem. Biophys. Res. Commun.,* 289:150-154 (2001)); colorimetric detection using metal-sensitive indicators (Tomita, et. al., *Nat. Protocols,* 3(5):877-82 (2008); Goto, et al., *BioTechniques,* 46(3):167-71 (2009)); bioluminescence through pyrophosphate conversion (Gandelman, et al., *PLoS One,* 5: e14155 (2010)); or detection via change in pH due to amplification in weakly-buffered conditions (Pourmand, et. al., *PNAS,* 103(17):6466-70 (2006); U.S. Pat. No. 7,888,015; and U.S. patent application Ser. No. 13/799, 995.

After the chromatin has been fragmented and tagged to produce tagged fragments of genomic DNA, at least some of the adaptor tagged fragments are sequenced to produce a plurality of sequence reads. The fragments may be sequenced prior to or after the ligation step.

Additionally or alternatively, the fragments may be sequenced prior to or after the amplification step using any convenient method.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

Sequencing can be carried out by any method known in the art including, but not limited to, sequencing by hybridization, sequencing by ligation or sequencing by synthesis. Sequencing by ligation includes, but is not limited to, fluorescent in situ sequencing (FISSEQ). Sequencing by synthesis includes, but is not limited to, reversible terminator chemistry (i.e. Illumina SBS).

The present invention further provides a method for analyzing chromatin in situ in a fixed biological sample. The method comprising (a) preparing a genomic library as described herein; and (b) sequencing all or a portion of the tagged fragments to produce a plurality of sequence reads. The information obtained from the sequence reads can be used for making an epigenetic map of the genome, or a region thereof, of the fixed sample in situ by mapping the information to the genome, or region thereof.

The present disclosure also provides a method for analyzing the three-dimensional structure of a polynucleotide from a fixed biological sample in situ, comprising: preparing a genomic library as described herein; and using the molecular tags to analyze the three-dimensional structure of the polynucleotide. In some embodiments, the insertional enzyme can comprise two or more enzymatic moieties, which may be optionally linked together. The enzymatic moieties can be linked by using any suitable chemical synthesis or bioconjugation methods. For example, the enzymatic moieties can be linked via an ester/amide bond, a thiol addition into a maleimide, Native Chemical Ligation (NCL) techniques, Click Chemistry (i.e., an alkyne-azide pair), or a biotin-streptavidin pair. In some embodiments, each of the enzymatic moieties can insert a common sequence into the polynucleotide. The common sequence can comprise a common barcode. The enzymatic moieties can comprise transposases or derivatives thereof. In some embodiments, the genomic DNA may be fragmented into a plurality of fragments during the insertion. The fragments comprising the common barcode can be determined to be in proximity in the three-dimensional structure of the polynucleotide.

In some embodiments, DNA fragments corresponding to one or more regions of a genome (e.g., 2 or more, 10 or more, 50 or more, 100 or more, up to 1,000 or more regions) may be enriched, i.e., selected, by hybridization prior to sequencing. In these embodiments, the entire library does not need to be sequenced. Depending on the desired result and length of the selected region (if a selection step has been performed), this step of the method may result in at least 1,000 sequencing (e.g., at least 10,000, at least 100,000, at least 500,000, at least $10^6$, at least $5 \times 10^6$, up to $10^7$ or more sequencing reads). The sequence reads are generally stored in computer memory.

Some embodiments of the methods involve making an epigenetic map of a region of the genome of the fixed biological sample in situ. This step may be done by sequencing all or a portion of the tagged fragments of genomic DNA and mapping information obtained from the sequence reads to the region. In these embodiments, the sequence reads are analyzed computationally to produce a number of numerical outputs that are mapped to a representation (e.g., a graphical representation) of a region of interest. Many types of information may be mapped, including, but not limited to: (i) cleavage sites for the transposase; (ii) the sizes of the fragments produced in step a); (iii) fragment length; (iv) the positions of sequence reads of a defined range in length; and (v) sequence read abundance.

The resultant epigenetic map can provide an analysis of the chromatin in a region of interest. For example, depending on which information is mapped, the map can show one or more of the following: a profile of chromatin accessibility along the region; DNA binding protein (e.g., transcription factor) occupancy for a site in the region; nucleosome-free DNA in the region; positioning of nucleosomes along the region; and a profile of chromatin states along the region. In some embodiments, the method may further comprise measuring global occupancy of a binding site for the DNA binding protein by, e.g., aggregating data for one DNA binding protein over a plurality of sites to which that protein binds. In certain instances, the map can also be annotated with sequence information, and information about the sequence (e.g., the positions of promoters, introns, exons, known enhancers, transcriptional start sites, untranslated regions, terminators, etc.) so that the epigenetic information can be viewed in context with the annotation.

In certain embodiments, the epigenetic map can provide information regarding active regulatory regions and/or the transcription factors that are bound to the regulatory regions. For example, nucleosome positions can be inferred from the lengths of sequencing reads generated. Alternatively, transcription factor binding sites can be inferred from the size, distribution and/or position of the sequencing reads generated. In some embodiments, transcription factor binding sites can be inferred from sequencing reads generated. In other embodiments, transcription factors can be inferred from sequencing reads generated.

The method described above may also be used as a diagnostic (which term is intended to include methods that provide a diagnosis as well as methods that provide a prognosis). These methods may comprise, e.g., analyzing chromatin from a patient using the methods described herein to produce an epigenetic map; and providing a diagnosis or prognosis based on the epigenetic map.

The method set forth herein may be used to provide a reliable diagnostic to any condition associated with altered chromatin or DNA binding protein occupancy. The method can be applied to the characterization, classification, differentiation, grading, staging, diagnosis, or prognosis of a condition characterized by an epigenetic pattern (e.g., a pattern of chromatin accessibility or DNA binding protein occupancy). For example, the method can be used to determine whether the epigenetic map of a sample from an individual suspected of being affected by a disease or condition is the same or different compared to a sample that is considered "normal" with respect to the disease or condition. In particular embodiments, the method can be directed to diagnosing an individual with a condition that is characterized by an epigenetic pattern at a particular locus in a test sample, where the pattern is correlated with the condition. The methods can also be used for predicting the susceptibility of an individual to a condition.

Exemplary conditions that are suitable for analysis using the methods set forth herein can be, for example, cell proliferative disorder or predisposition to cell proliferative disorder; metabolic malfunction or disorder; immune malfunction, damage or disorder; CNS malfunction, damage or disease; symptoms of aggression or behavioral disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

In some embodiments, the method can provide a prognosis, e.g., to determine if a patient is at risk for recurrence. Cancer recurrence is a concern relating to a variety of types of cancer. The prognostic method can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

In yet another aspect, the present disclosure provides kits that contain reagents for practicing the subject methods, as described herein. The subject kits can comprise a transposase and transposon tags, and a transposase reaction buffer, wherein the components of the kit are configured such that, combining the reaction buffer, transposase and adaptors with a fixed biological sample results in the production of adaptor-tagged fragments of genomic DNA.

In some cases, the kit can comprise an insertional enzyme comprising an affinity tag; and an insert element comprising a nucleic acid, wherein said nucleic acid comprises a pre-determined sequence. The insertional enzyme can be, for example, a transposase. The insertional enzyme can also comprise two or more enzymatic moieties that are linked together. In some cases, the affinity tag can be an antibody. The antibody can bind to a transcription factor, a modified nucleosome, or a modified nucleic acid. Examples of modified nucleic acids include, but are not limited to, methylated or hydroxymethylated DNA. In other cases, the affinity tag can be a single-stranded nucleic acid (e.g. ssDNA, ssRNA).

The kit may optionally contain other components, for example: PCR primers, PCR reagents such as polymerase, buffer, nucleotides etc., as described above. The various components of the kit may be present in separate containers or certain compatible components may be precombined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The terms "next-generation sequencing" or "high-throughput sequencing" refer to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or single-molecule fluorescence-based method commercialized by Pacific Biosciences.

The term "barcode sequence" or "molecular barcode," as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "chromatin," as used herein, refers to a complex of molecules including proteins and polynucleotides (e.g., DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA.

The term "treating," as used herein, refers to combining under conditions (e.g., a suitable temperature, time and conditions) that result in a reaction, (e.g., cleavage).

The term "transcription factor", as used herein, refers to any polypeptide that may act by itself or in combination with at least one other polypeptide to regulate gene expression levels. The term includes, but is not limited to, polypeptides that directly bind DNA sequences. Transcription factors can either increases or suppress expression levels. Examples of transcription factors include, but are not limited to Myc/Max, AP-1 (Jun, Fos, ATF), CREB, SMAD, HIF, ETS, ERG, ELK, STAT, estrogen receptor (ER), androgen receptor (AR), glucocorticoid receptor (GR), progesterone receptor (PR), NFKB, p53, OCT, SOX and PAX. The transcription factor may be a transcription factor identified by sequence analysis or a naturally-occurring reading frame sequence that has not been previously characterized as a transcription factor. The polypeptide may also be an artificially generated or chemically or enzymatically modified polypeptide.

The term "tagged fragments," as used herein, refers to polynucleotide fragments that are attached to tags.

The term "region," as used herein, refers to a contiguous length of nucleotides in a genome of an organism. A chromosomal region may be in the range of 1 bp to the length of an entire chromosome. In some instances, a region may have a length of at least 200 bp, at least 500 bp, at least 1 kb, at least 10 kb or at least 100 kb or more (e.g., up to 1 Mb or 10 Mb or more). The genome may be from any eukaryotic organism, e.g., an animal or plant genome such as the genome of a human, monkey, rat, fish or insect.

The term "epigenetic map," as used herein, refers to any representation of epigenetic features, e.g., sites of nucleosomes, nucleosome-free regions, binding sites for transcription factors, etc. A map can be physically displayed, e.g., on a computer monitor.

The term "mapping information," as used herein, refers to assembling experimentally-obtained information about an area to a physical map of the area.

The term "chromatin accessibility," as used herein, refers to how accessible a nucleic acid site is within a polynucleotide, such as in genomic DNA, i.e., how "open" the chromatin is. A nucleic acid site associated with a polypeptide, such as with genomic DNA in nucleosomes, is usually inaccessible. A nucleic acid site not complexed with a polypeptide is generally accessible, such as with genomic DNA between nucleosomes (with the exception of nucleic acid sites complexed with transcription factors and other DNA binding proteins).

EXAMPLES

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

Demonstration of In Situ Genomic Library Construction

To demonstrate in situ genomic sequencing library construction, we have used the following technique on multiple cell lines [HeLa, GM12878, IMR90, primary neuron culture] and in mouse brain slice.

A. Fix and Permeabilize Cells:
1. Fix with cold 4% PFA for 10 min at RT.
2. Wash with 5 min 1× PB+100 mM glycine to quench fixation.
3. Wash 2× 5 min with 1× PBS
4. Permeabilize with 1× PBS+0.5% Triton-X for 30 minutes.

B. Adaptor Insertion:
1. Prepare 2× Tn5 buffer:

| Component | Amount (µl) | Final concentration |
| --- | --- | --- |
| Nuclease-free H2O | 710 | |
| 10x PBS | 60 | 0.6x |
| 1M Tris-HCl pH 8.0 | 20 | 20 mM |
| 1M MgCl2 | 10 | 10 mM |
| DMF | 200 | 20% |
| Total | 1000 | |

2. Prepare 50 uL Tn5 reaction mixes (1 reaction per sample):

| Component | Amount (µl) | Final concentration |
| --- | --- | --- |
| Nuclease-free H2O | 23 | |
| 2x Tn5 Buffer | 25 | 1x |
| Tn5 | 2 | |
| Total | 50 | |

3. Incubate reactions at 37° C. for 1 hour
4. Wash samples 3× 15 m in 1× PBS+50 mM EDTA at 60° C.

C. Adaptor Replacement:
1. Prepare 10× annealing buffer:

| Component | Amount (mL) | Final concentration |
| --- | --- | --- |
| Nuclease-free H2O | 16 | |
| 20x TE pH 7.5 | 20 | 10x |
| 5M NaCl2 | 4 | 500 mM |
| Total | 40 | |

2. Anneal adaptor replacement hairpins separately at 10 uM in 1× annealing buffer. Ramp from 95 C to RT at 0.1 C/s.
3. Combine hairpins at individual concentrations of 500 nM in 4× SSC.
4. Incubate samples with 500 nM hairpins at 37° C. for 2 h.

D. Gap Fill and Ligation:
1. Prepare 50 uL ligation mixes (1 per sample):

| Component | Amount (µl) | Final concentration |
| --- | --- | --- |
| Nuclease-free H2O | 35 | |
| 10x Ampligase buffer | 5 | 1x |
| NEB T4 pol (3 U/uL) | 2.5 | 0.15 U/uL |
| Ampligase (5 U/uL) | 6.25 | 0.625 U/uL |
| 10 mM dNTPs | 1.25 | 250 uM |
| Total | 50 | |

2. Incubate samples in ligation mix for 30 m at 37° C.
3. Wash samples twice in 1× PBS.

E. RCA Primer Hybridization and Reaction
1. Incubate RCA primer with sample at 37° C. for 3 hours:

| Component | Amount (µl) | Final concentration |
| --- | --- | --- |
| Nuclease-free H2O | 59.5 | |
| Formamide, 100% | 30 | 30% |
| SSC buffer, 20x | 10 | 2x |
| RCA primer, 100 µM | 0.5 | 0.5 µM |
| Total | 100 | |

2. Wash once with the following:

| Component | Amount (µl) | Final concentration |
| --- | --- | --- |
| Nuclease-free H2O | 59.5 | |
| Formamide, 100% | 30 | 30% |
| SSC buffer, 20x | 10 | 2x |
| Total | 100 | |

3. Wash twice with 1× PBS
4. Prepare RCA reaction mix and incubate with samples at 30° C. overnight

| Component | Amount (µl) | Final concentration |
| --- | --- | --- |
| Nuclease-free H2O | 76.5 | |
| Phi29 buffer, 10x | 10 | 1x |
| dNTP, 10 mM | 2.5 | 250 µM |
| Aminoallyl dUTP, 4 mM | 1 | 40 µM |
| Phi29 polymerase (10 U/uL) | 10 | 1 U/µl |
| Total | 100 | |

F. Visualization:
1. Wash with PBS, aspirate and add the following for 45 min at RT:

| Component | Amount (μl) | Final concentration |
|---|---|---|
| Nuclease-free H2O | 140 | |
| Formamide, 100% | 20 | 10% |
| SSC buffer, 20x | 40 | 4x |
| Rolonies hybridization probe, 100 μM | 0.2 | 0.1 μM |
| Total | 200 | |

2. Aspirate and wash 2× 5 m with 1× PBS
3. Stain the nucleus of the neurons for 10 min at RT with DAPI diluted 1:1000 in PBS 1×. Wash with PBS
4. Image the rolonies G. Gelation, Digestion, Crosslinking:
This section is loosely related to the ExM 1.0 Cultured Cell Protocol, V1.4 (see expansionmicroscopy.org)
1. Prepare the following monomer solution:

| Component | Amount (μl) | Final concentration |
|---|---|---|
| Nuclease-free H2O | 160 | |
| PBS, 10x | 20 | 10% |
| 40% bis/acrylamide (19:1) | 20 | 4x |
| Total | 200 | |

2. Remove liquid from wells.
3. Remove top section from Gracelabs dish using supplied tool and peel off silicone gasket.
4. Flank cells with scotch tape (two pieces each side).
5. Add 10% APS and 10% TEMED to monomer solution, each to a concentration of 0.1%
6. Add ~20 uL gelation solution per well in region and then sandwich with glass coverslip.
7. Gel for 1 hour at 37 C
8. Prepare 1× digestion buffer (50 mM Tris pH 8.0, 1 mM EDTA, 0.5% Triton X-100)
9. Add Protinase K at 1:100 to digestion buffer
10. Incubate gels in digestion buffer overnight at room temperature.
11. Wash 2× 5 m with 1× PBS
12. To cross-link rollonies molecules containing aminoallyl dUTP, wash gently with PBS, and then incubate the following for 2 hr at RT:

| Component | Amount (μl) | Final concentration |
|---|---|---|
| PBS, 1x | 98 | ~1x |
| Reconstituted BS(PEG)9, 250 mM | 2 | 5 mM |
| Total | 200 | |

13. Wash with PBS 1× 5 min, aspirate and add 1 M Tris pH 8.0 for 45 min at RT.
14. Wash with PBS 2× 5 min H. Sequencing
The rollonies can now be sequenced as described in Lee et al., *Science*. 343, 1360-3 (2014).

Figures 2A, 2B, 2C:
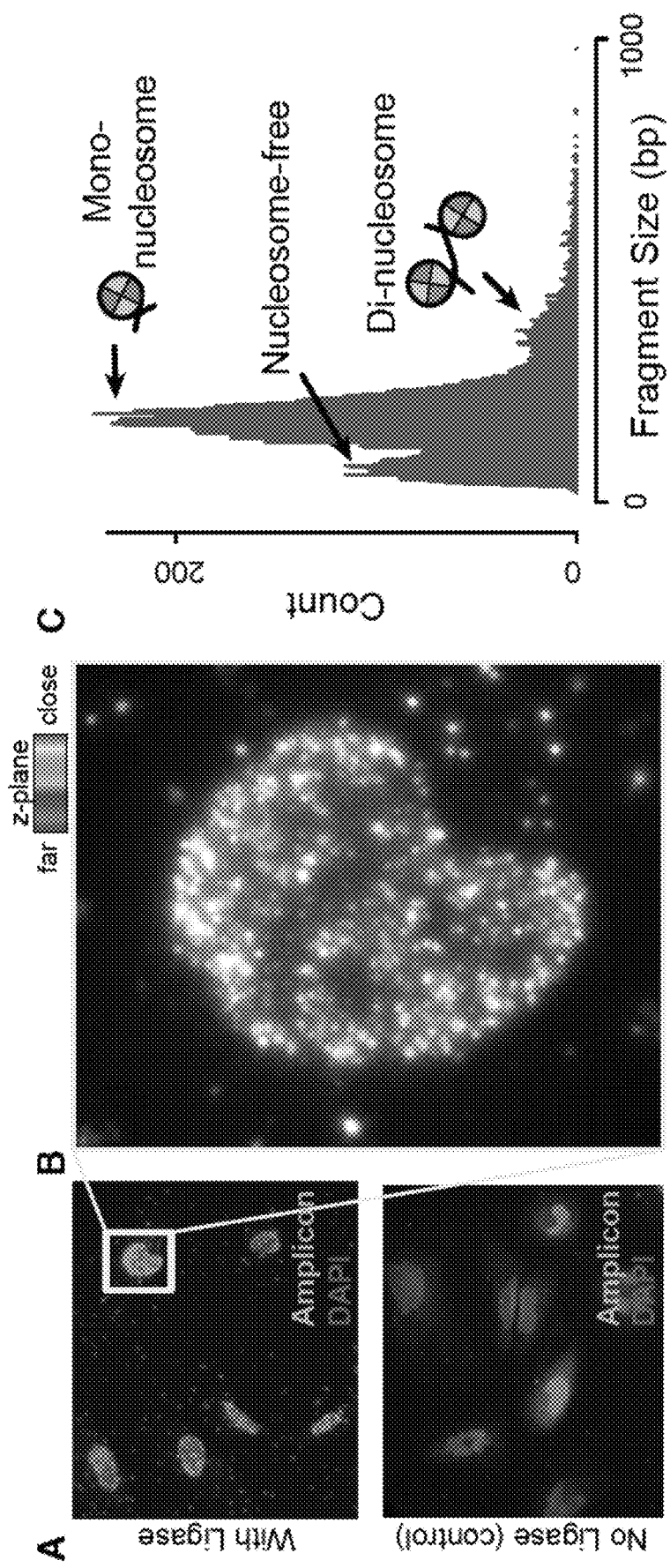
FIG. 2A through FIG. 2C: Demonstration of in situ genomic library construction from accessible chromatin. (A) HeLa cells with in situ amplified ATAC-seq fragments (green) and DAPI (blue). Top: PFA-fixed HeLa cells treated using the protocol disclosed (see Demonstration of in situ genomic library construction); Bottom: control sample omitting the gap-fill & ligation step, demonstrating that all amplified DNA is generated from transposase-tagged genomic fragments. In situ amplicons are visualized using fluorescent in situ DNA hybridization (FISH) against an adapter sequence. (B) A single HeLa nucleus, demonstrating that spatial information corresponding to each fragment is preserved and can be quantified; each pixel is colored by the maximum fluorescence at each z-image. (C) Paired end sequencing of in situ amplified material on an Illumina HTS sequencer provides a fragment-size distribution similar to previous ATAC-seq studies.
Figure 3:
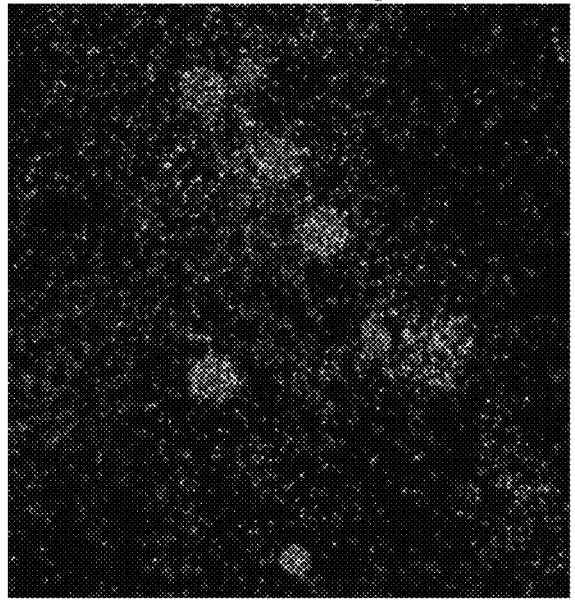
FIG. 3: Demonstration of in situ ATAC-seq library construction in diverse cell types. Transposase accessible genomic sequencing libraries were constructed via the method provided herein in multiple fixed cell lines (HeLa, IMR90, and primary neuron culture).
Figure 3:
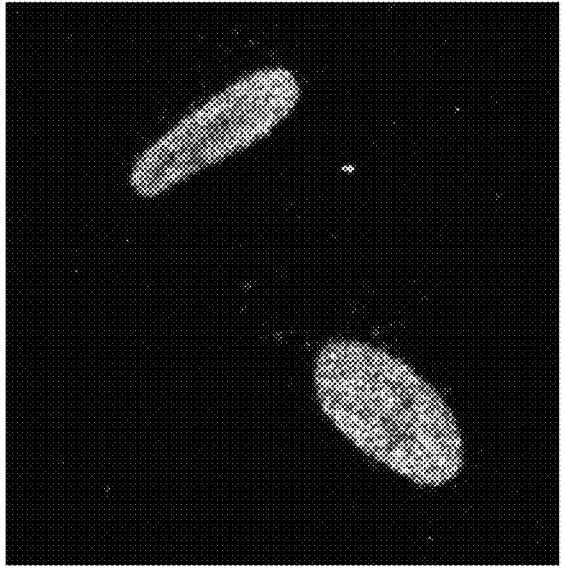
Figure 3:
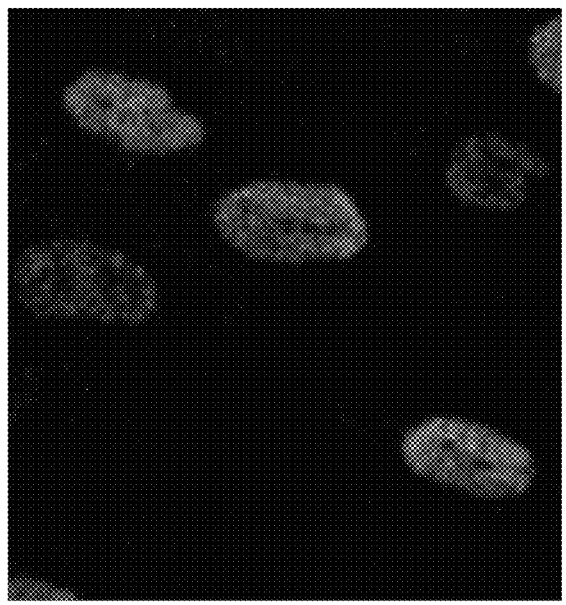

The In Situ Epigenome
FIG. 1 depicts in situ ATAC followed by DNA amplification to form 3D amplicon libraries within fixed cells. Here, fixed cells are treated using Tn5 transposase loaded with custom DNA sequence adapters. After transposition, dumbbell adapter sequences are hybridized and ligated onto transposed DNA fragments (FIG. 1B). The resulting circular product is amplified using rolling circle amplification (RCA) (FIG. 2) and sequenced in situ using sequencing by ligation (ABI SOLiD) (FIG. 3).

These methods provide the first in situ sequencing epigenomics method. This approach represents a stark departure from traditional epigenomics tools in that the epigenome is uniquely measured in its native context (i.e., in situ). This approach has several advantages enabling fundamentally new insights into basic and applied avenues of biological research, including: (1) an in situ spatially resolved map of regulatory elements, which provides new insights in the 3D epigenomic structures within single-cells and therefore the genesis of gene expression; (2) a natural platform for combining '-omic' methods, which, unlike ensemble methods, in situ approaches retain RNA and protein molecules within the cell and in situ sequencing may be adapted to spatially resolve the epigenome in combination with the transcriptome and/or protein binding (analogous to scChIP-seq) within the same single-cell; and (3) application to tissues wherein the epigenome can be interrogated without tissue dissociation and thus enable insights into the epigenomics of tissue structures and cell-cell interactions.

Super Resolution In Situ ATAC-Seq with Expansion Microscopy

Super-resolution expansion microscopy (ExM) and in situ ATAC-seq (ATAC-ExSeq) are combined and, thus, enable a structural understanding of chromatin configurations across single cells. Physical expansion allows densely packed cellular DNA to be resolved spatially in a high-throughput manner, a fundamental requirement for in situ sequencing.

Additionally, the expanded environment is 99% water, facilitating enzyme access and reducing molecular crowding, both of which improve enzymatic yield of sequencing reactions.

Figure 4A:
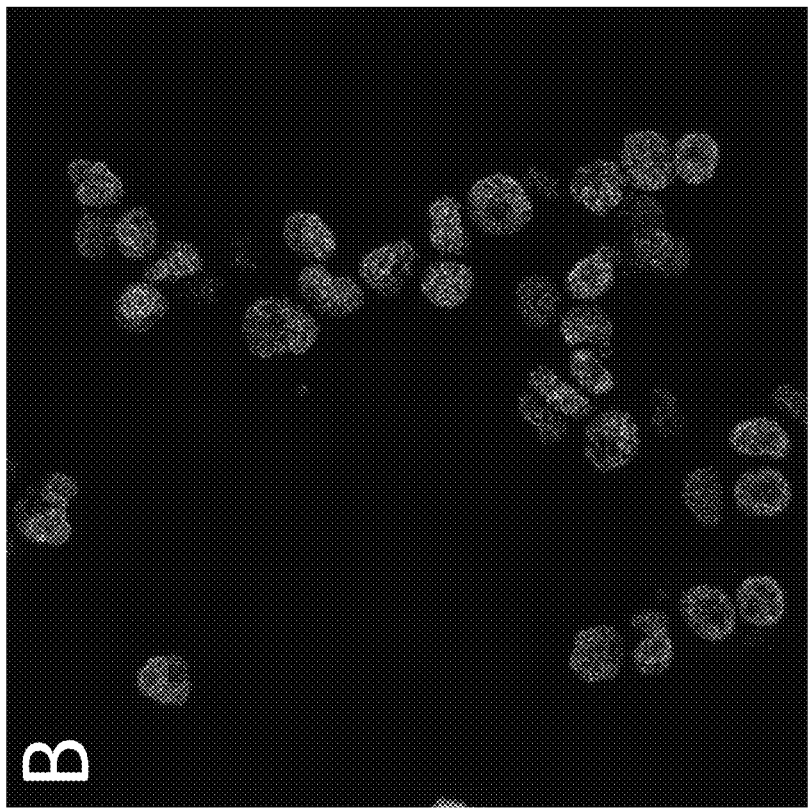
FIG. 4A and FIG. 4B: Demonstration of in situ ATAC-seq library construction in fixed suspension cells via the method provided herein with the following modification: the cells were embedded in a 5% acrylamide hydrogel immediately following permeabilization.
Figure 4B:
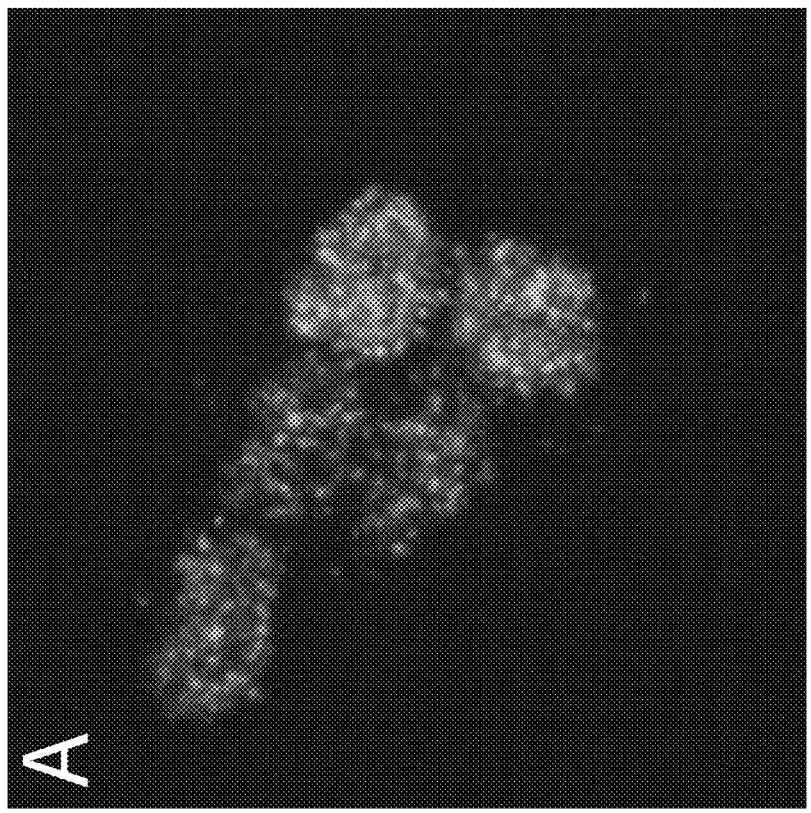
Figure 5:
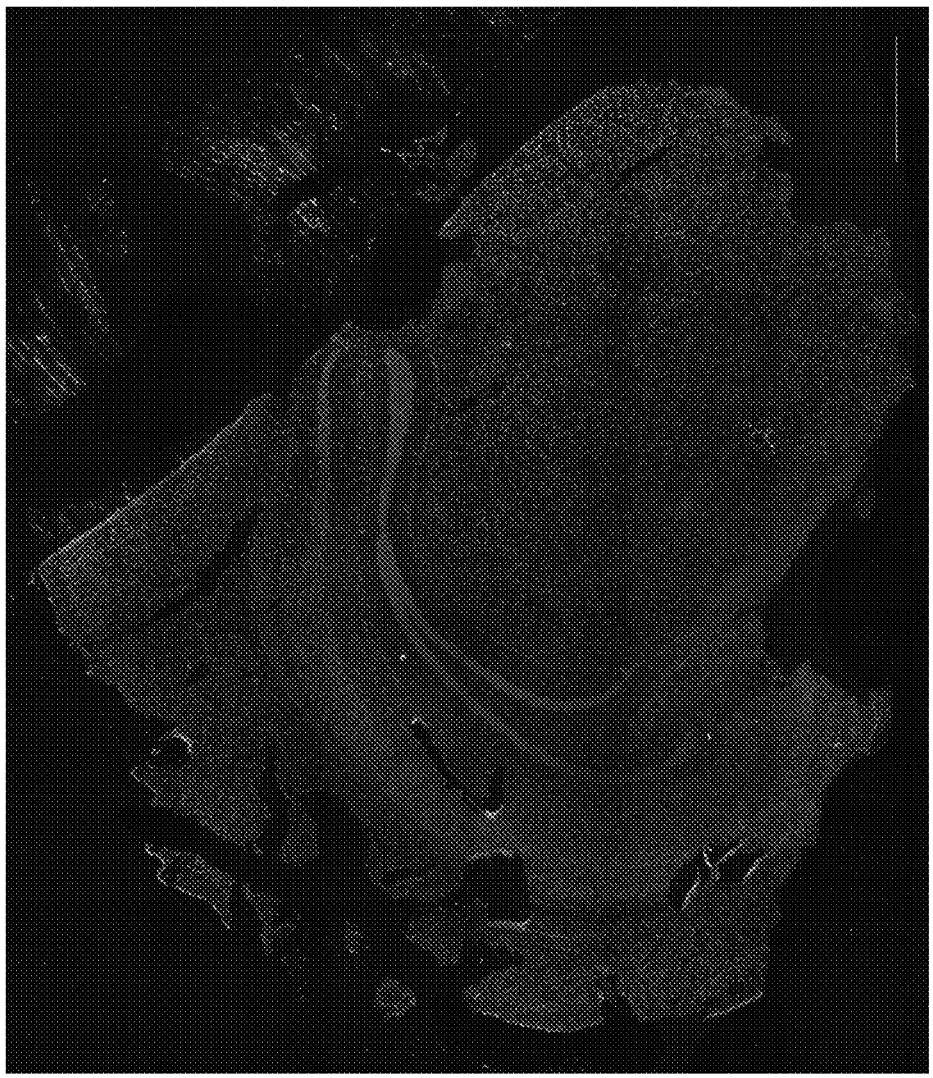
FIG. 5: Demonstration of in situ ATAC-seq library construction in coronal section of mouse brain via the method provided herein, showing whole-slice coverage [DAPI=blue; library hybridization probe=green].
Figures 6A, 6B:
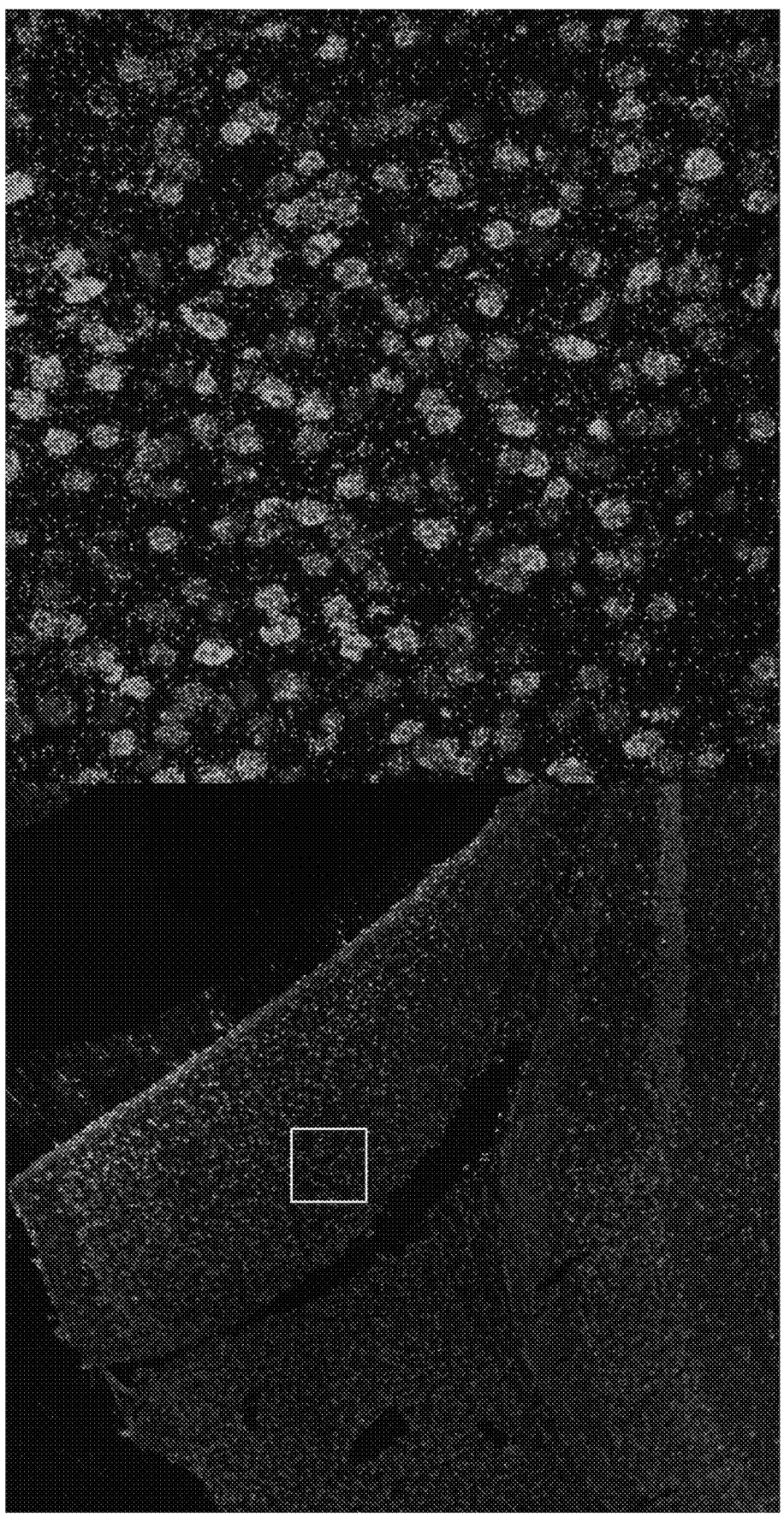
FIG. 6A and FIG. 6B: High resolution zoom of in situ ATAC library in mouse cortex.
Figure 7:
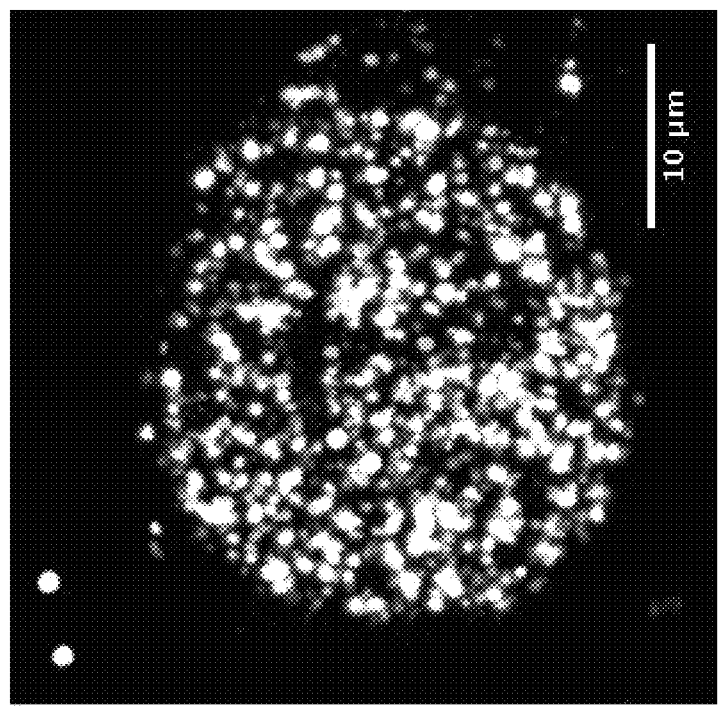
FIG. 7: Demonstration of one base of 4-color sequencing by ligation (SOLiD SBL) of a barcoded in situ ATAC library prepared in HeLa cells using the method described herein; here, a barcode and sequencing primer site is included in the hairpin loop.
Figure 8:
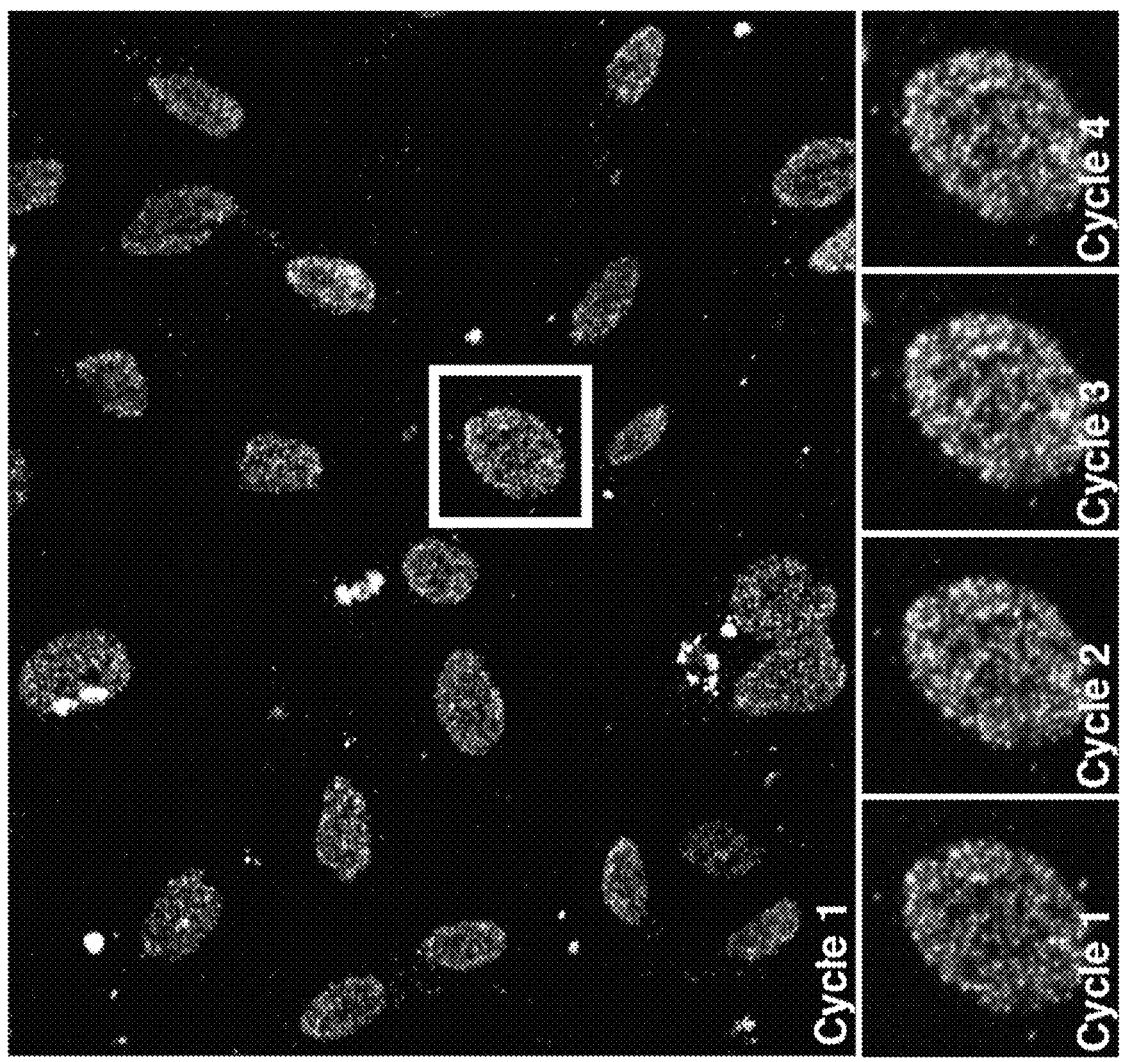
FIG. 8: In situ sequencing of an in situ ATAC-seq library prepared in HeLa cells using the method described herein. Top: Imaging after first cycle incorporation using 4-color sequencing by ligation (SOLiD SBL). Bottom: Highlighted cell after four cycles of SBL sequencing.
Figure 10A:
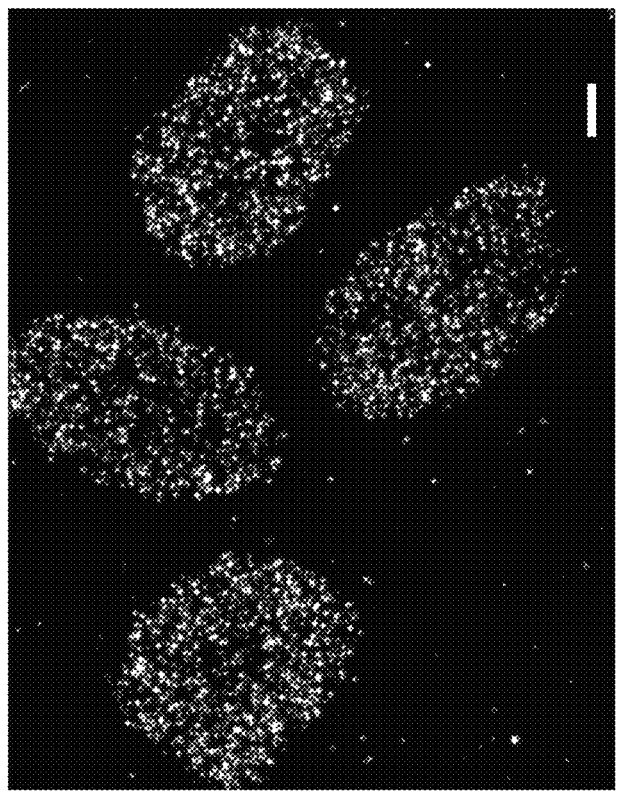
FIG. 10A and FIG. 10B: Expanded in situ genomic library preps. The non-expanded sample on the left in the figure (FIG. 10A) was produced using the protocol described in "Demonstration of in situ genomic library construction", with the following deviation: the sample was treated with 0.1 N HCl for 5 minutes and washed twice with PBS before adaptor insertion. The expanded sample on the right in the figure (FIG. 10B) was produced using the protocol described in "Demonstration of in situ genomic library construction", with the following deviations: (i) the sample was treated with 0.1 N HCl for 5 minutes and washed twice with PBS before adaptor insertion, (ii) the RCA primer contained LNA bases and a 5' Acrydite modification, and (iii) the samples were embedded in a swellable hydrogel, digested, expanded, re-embedded in 4% polyacrylamide, and passivated (as described in patent US20160304952A1 titled 'In situ nucleic acid sequencing of expanded biological samples') before the overnight RCA reaction. Scale bars are 10 μm.
Figure 10B:
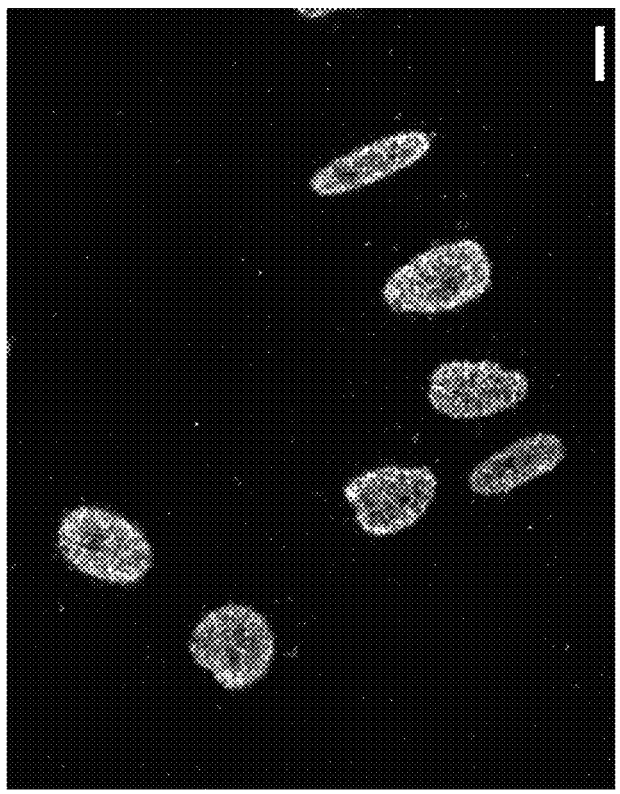
Figure 11A:
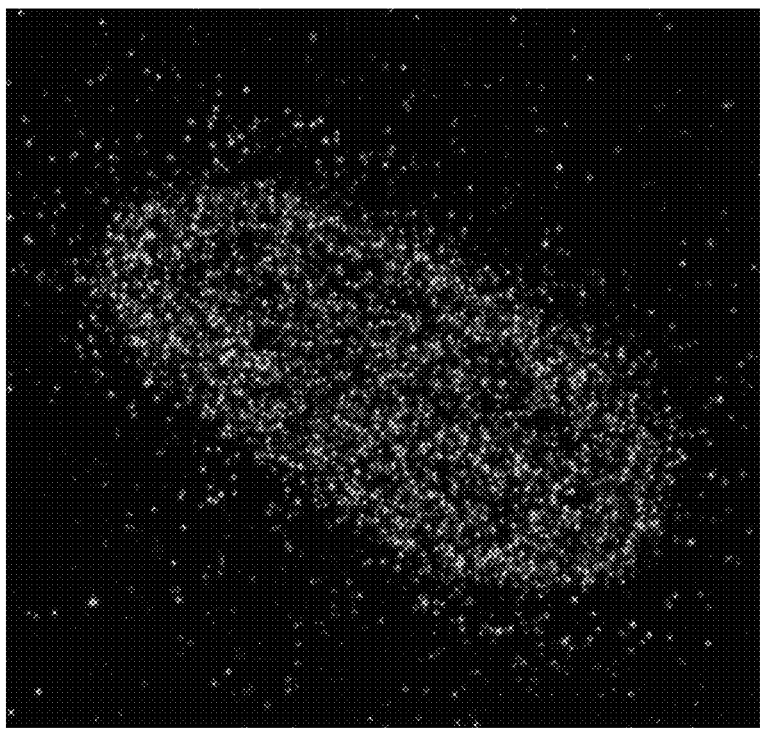
FIG. 11A and FIG. 11B: Demonstration of whole-genome [not ATAC] library construction in expanded HeLa culture (hybridization probe against clusters). [HeLa cells were permeabilized in swellable polymer, digested, expanded, passivated and re-embedded, and then subjected to library construction protocol. By digesting the sample first, we ensure an unbiased library construction, cf. ATAC which requires a relatively unperturbed sample].
Figure 11B:
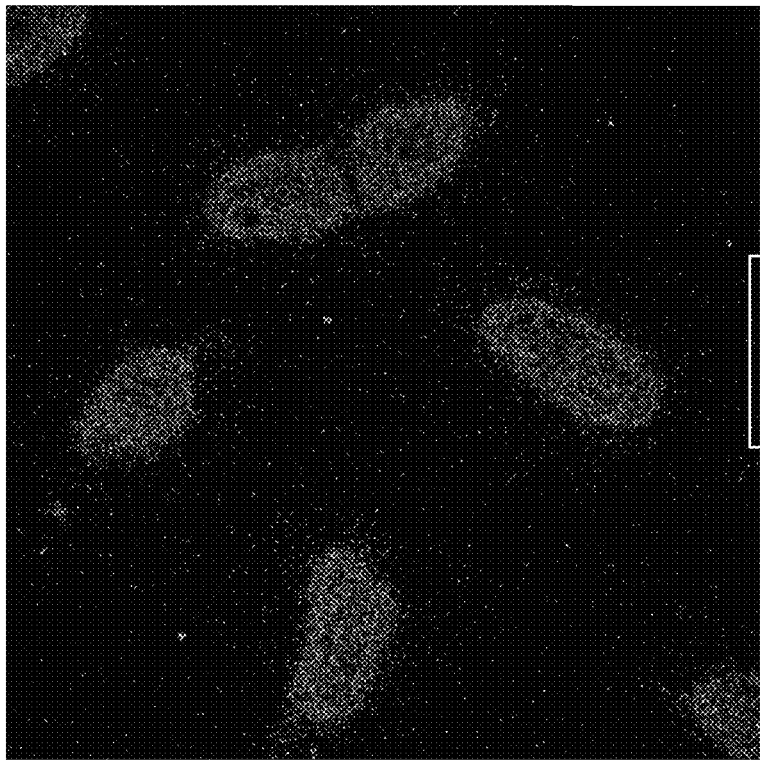
Figures 12A, 12B:
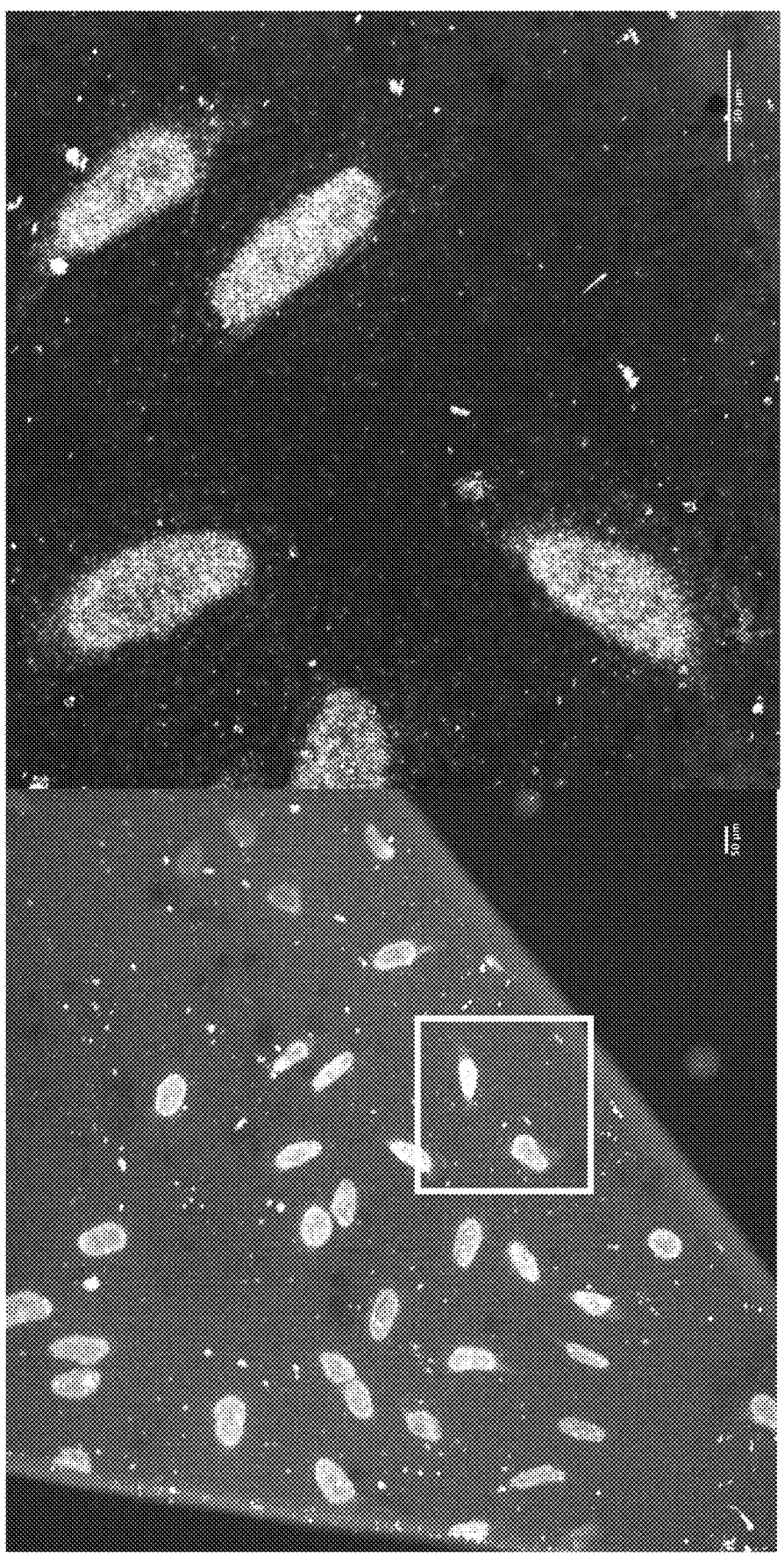
FIG. 12A through FIG. 12D: First base of in situ sequencing for whole-genome sequencing library prepared in expanded HeLa culture as described in FIG. 11.
Figures 12C, 12D:
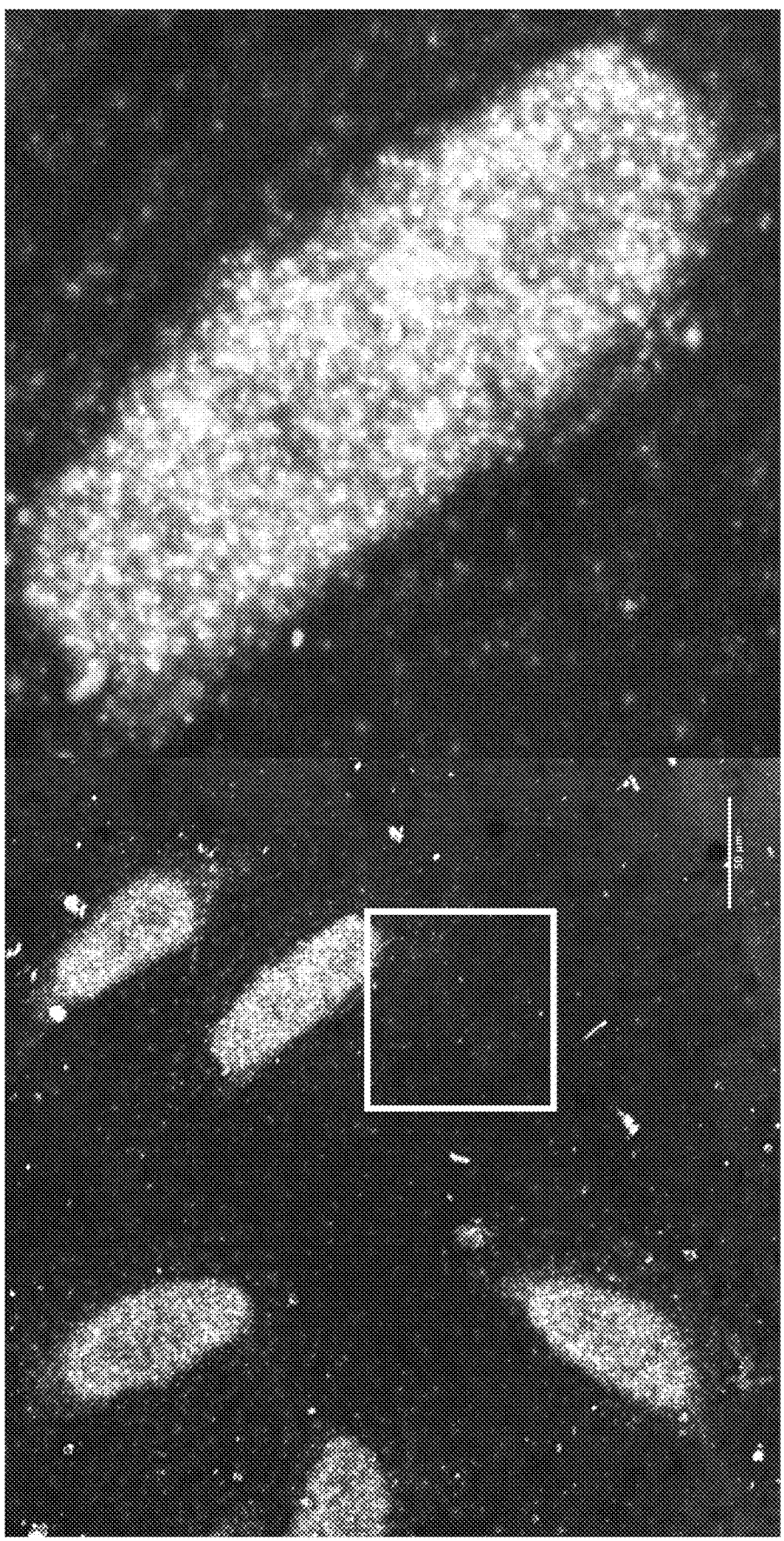

Expansion ATAC Imaging
FIG. 4 depicts images from the combination of ExM and ATAC-seq. Here, Tn5 was loaded with DNA containing a fluorescent dye, transposed into fixed HeLa cells and expanded. After expansion and staining with DAPI, HeLa cells were imaged with a conventional point-scanning confocal. After expansion, ATAC specific fluorescence was retained and high-resolution co-localization with features in DAPI was observed, demonstrating compatibility between expansion and in situ ATAC methods.

Expansion for High-Density In Situ Epigenomics
Physical expansion enables improved enzymatic efficiencies and spatial resolution of regulatory features. Without expansion, the amplicons space-fill the nucleus, preventing further improvement in yield. Conversely, ~4× linear expansion as implemented in standard ExM protocols enables ~60 fold volumetric increase, corresponding to ~60,000 (versus ~1,000 without expansion) spatially-resolvable diffraction limited spots in a 100 um$^3$ nucleus. Therefore, ATAC-ExSeq enables high yield and super-resolved sequencing of the epigenome.

In one embodiment, molecules of interest are anchored to the hydrogel to enable selective retention and expansion. To anchor ATAC fragments, an amine reactive acrylamide moiety (acryloyl-X) was incorporated to the transposase DNA adapter by synthesizing an internal amine within the Tn5 DNA adapter. Subsequent Tn5 loading and transposition will incorporate the acrylamide moiety on all transposed fragments.

Alternatively, to anchor ATAC fragments, Label-X can be incorporated to the transposase DNA adapter and enable isotropic expansion of DAPI staining in cells and tissues.

ATAC-ExSeq for Super Resolution Chromatin Interactions

The resolution of RCA amplicons in the expanded state is linearly increased by the expansion factor, thus, ~4 fold linear expansion allows for ~60 nm resolution during sequencing. Thus, at 60 nm resolution, it will be possible to study variability across topologically associated domains (TADs) genome wide.

Additionally, iterated expansion allows for expansion factors up to 20× and a resolution of ~20 nm. 20× expansion can resolve even more fragments per cell and thus, in addition to chromatin accessibility, it will allow for methods for transposition after de-proteinization of DNA for spatial sequencing of the whole genome. This additional resolution will enable insight into chromatin compaction and provide a low-resolution map of enhancer-promoter connectivity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing and amplifying a genomic DNA library in situ in a fixed and permeabilized biological sample, the method comprising (a) treating the fixed sample with an insertional enzyme complex comprising an insertional enzyme and at least two adaptor molecules comprising additional sequences for circularization, amplification, detection and/or sequencing resulting in one or more tagged fragments of genomic DNA; (b) circularizing the one or more tagged fragments of genomic DNA by hairpin hybridization and ligation; and (c) amplifying the one or more circularized tagged fragments of genomic DNA.

2. The method according to claim 1, wherein the circularization further comprises oligonucleotide displacement and gap repair.

3. The method according to claim 1, wherein the insertional enzyme is a transposase.

4. The method of according to claim 3, wherein the transposase is a Tn5 transposase.

5. The method according to claim 3, wherein the transposase is a MuA transposase.

6. The method according to claim 1, wherein the adaptors comprise unmodified DNA oligonucleotides.

7. The method according to claim 1, wherein the complex adaptors comprise chemically modified DNA oligonucleotides.

8. The method according to claim 1, wherein the method further comprises the step of detecting the amplified product.

9. The method according to claim 8, wherein a fluorescent hybridization probe complementary to an adapter sequence is used for detection.

10. The method according to claim 1, wherein the method further comprises the step of quantifying the amplification product.

11. The method according to claim 10, wherein a fluorescent hybridization probe complementary to a target sequence of genomic DNA is used for detection.

12. The method according to claim 1, wherein the method further comprises the step of sequencing the amplified product.

13. The method according to claim 12, wherein the one or more tagged genomic DNA fragments are sequenced.

14. The method according to claim 12, wherein a unique molecular identifier ligated to the one or more fragments is sequenced.

15. The method according to claim 14, wherein the unique molecular identifier is contained in a hairpin.

16. The method according to claim 14, wherein the unique molecular identifier is sequenced.

17. The method according to claim 1, wherein the sample is embedded in a swellable or unswellable material:
   prior to step (a);
   after step (a);
   after step (b); or
   after step (c).

18. The method according to claim 1, wherein the genomic DNA library is constructed from accessible chromatin.

19. The method according to claim 1, wherein the genomic DNA library is constructed from the whole genome.

* * * * *